(12) United States Patent
Mitchell et al.

(10) Patent No.: US 6,340,463 B1
(45) Date of Patent: Jan. 22, 2002

(54) IDENTIFICATION OF ANTIGENIC PEPTIDE SEQUENCES

(75) Inventors: William M. Mitchell; Charles W. Stratton, both of Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/025,596

(22) Filed: Feb. 18, 1998

Related U.S. Application Data

(63) Continuation-in-part of application No. 08/911,593, filed on Aug. 14, 1997, now abandoned.
(60) Provisional application No. 60/023,921, filed on Aug. 14, 1996.

(51) Int. Cl.[7] .................. A61K 39/118; A61K 49/00; A61K 39/395; C12N 1/00; C07K 14/00
(52) U.S. Cl. .................. 424/263.1; 424/9.1; 424/9.2; 424/130.1; 424/184.1; 424/185.1; 424/190.1; 424/191.1; 424/234.1; 424/278.1; 435/41; 435/243; 530/300
(58) Field of Search .................. 424/9.1, 9.2, 130.1, 424/184.1, 185.1, 190.1, 191.1, 234.1, 263.1, 278.1; 435/41, 243; 530/300

(56) References Cited

U.S. PATENT DOCUMENTS 5,869,608 A * 2/1999 Caldwell et al. ............ 530/350

FOREIGN PATENT DOCUMENTS

| WO | WO 93/19183 | 9/1993 | ........... C12N/15/46 |
|----|-------------|--------|----------------------|
| WO | WO 98/02546 | 1/1998 | ........... C12N/15/31 |

OTHER PUBLICATIONS

Leuken et al, "Localisation of amino acid sequence stretches containing a continuous epitope on the surface of the two Lathyrus ochrus isolectins", *Immunology Letters*, vol. 23, No. 3, pp. 223–226, Jan. 1990.*

Van Regenmortel, M.H.V., "Which Structural Features Determine Protein Antigenicity?", *Trends in Biochemical Sciences*, 11:36–39 (1986).

Karplus, P.A. and Schulz, G.E., "Prediction of Chain Flexibility in Proteins", *Naturwissenschaften*, 72:212–213 (1985).

Hopp, T.P. and Woods, K.R., "Prediction of Protein Antigenic Determinants from Amino Acid Sequences", *Proc. Natl. Acad. Sci.*, 78(6):3824–3828 (1981).

* cited by examiner

*Primary Examiner*—Rodney P Swartz
(74) *Attorney, Agent, or Firm*—Clark & Elbing, LLP

(57) ABSTRACT

Identification of linear amino acid antigenic sequences for the production of both polyclonal and monoclonal antibodies to defined antigenic domains is described. Also described are antigenic peptides identified by the described methods and antibodies thereto.

2 Claims, 4 Drawing Sheets

|   |   |   |   | SEQ ID NO. |
|---|---|---|---|---|
| CPN90-105 C. pneumoniae | C T G S A A - A N Y T T A V D - R P N | 93 |
| CTP89-105 C. trachomatis (mouse) | C T G D A D L T T A P T P A S - R E N | 94 |
| CTL91-106 C. trachomatis (L2) | C T T A T G N A A A P S T C T A R E N | 95 |
| CPS92-106 C. psitacci | C A S G T A - S N T T V A A D - R S N | 96 |

Fig. 2

| | | | SEQ ID NO. |
|---|---|---|---|
| CPN158-171 | *C. pneumoniae* | C F G V K G T T V N A N E - - - L P | 97 |
| CTP158-171 | *C. trachomatis* (mouse) | C F G R D E T A V A A D D - - - I P | 98 |
| CTL159-175 | *C. trachomatis* (L2) | C F G D N E N H A T V S D S K L V P | 99 |
| CPS160-172 | *C. psitacci* | C I G L A G T D F - A N Q - - - R P | 100 |

Fig. 3

| | | | SEQ ID NO. |
|---|---|---|---|
| CPN342-354 | *C. pneumoniae* | C Q I N K F K S R K A C G | 101 |
| CTP342-354 | *C. trachomatis* (mouse) | C Q I N K M K S R F A C G | 102 |
| CTL342-354 | *C. trachomatis* (L2) | C Q L N K M K S R K A C G | 103 |
| CPS342-354 | *C. psitacci* | C Q I N K F K S R F A C G | 104 |

Fig. 4

SEQUENCE LISTING

<160> NUMBER OF SEQ ID NOS: 118

<210> SEQ ID NO 1
<211> LENGTH: 14
<212> TYPE: PRT
<213> ORGANISM: Chlamydia pneumoniae

<400> SEQUENCE: 1

Lys Pro Lys Glu Ser Lys Thr Asp Ser Val Glu Arg Trp Ser
1               5                   10

<210> SEQ ID NO 2
<211> LENGTH: 11
<212> TYPE: PRT
<213> ORGANISM: Chlamydia pneumoniae

<400> SEQUENCE: 2

Ser Ser Asn Ser Ser Ser Ser Thr Ser Arg Ser
1               5                   10

<210> SEQ ID NO 3
<211> LENGTH: 8
<212> TYPE: PRT
<213> ORGANISM: Chlamydia pneumoniae

<400> SEQUENCE: 3

Gly Ser Lys Gln Gln Gly Ser Ser
1               5

<210> SEQ ID NO 4
<211> LENGTH: 8
<212> TYPE: PRT
<213> ORGANISM: Chlamydia pneumoniae

<400> SEQUENCE: 4

Gly Lys Ala Gly Gln Gln Gln Gly
1               5

<210> SEQ ID NO 5
<211> LENGTH: 9
<212> TYPE: PRT
<213> ORGANISM: Chlamydia pneumoniae

<400> SEQUENCE: 5

Pro Ser Glu Thr Ser Thr Thr Glu Lys
1               5

<210> SEQ ID NO 6
<211> LENGTH: 8
<212> TYPE: PRT
<213> ORGANISM: Chlamydia pneumoniae

<400> SEQUENCE: 6

Lys Pro Ala Asp Gly Ser Asp Val
1               5

<210> SEQ ID NO 7
<211> LENGTH: 11
<212> TYPE: PRT
<213> ORGANISM: Chlamydia pneumoniae

<400> SEQUENCE: 7

Asn Gly Gln Lys Lys Pro Leu Tyr Leu Tyr Gly

<210> SEQ ID NO 8
<211> LENGTH: 19
<212> TYPE: PRT
<213> ORGANISM: Chlamydia pneumoniae

<400> SEQUENCE: 8

Ser Asp Val Pro Asn Pro Gly Thr Thr Val Gly Ser Lys Gln Gln
1               5                   10                  15
Gly Ser Ser

<210> SEQ ID NO 9
<211> LENGTH: 15
<212> TYPE: PRT
<213> ORGANISM: Chlamydia pneumoniae

<400> SEQUENCE: 9

His Met Phe Asn Thr Glu Asn Pro Asp Ser Gln Ala Ala Gln Gln
1               5                   10                  15

<210> SEQ ID NO 10
<211> LENGTH: 9
<212> TYPE: PRT
<213> ORGANISM: Chlamydia pneumoniae

<400> SEQUENCE: 10

Asp Asp Ala Glu Asn Glu Thr Ala Ser
1               5

<210> SEQ ID NO 11
<211> LENGTH: 16
<212> TYPE: PRT
<213> ORGANISM: Chlamydia pneumoniae

<400> SEQUENCE: 11

Lys Glu Glu Asp Lys Lys Arg Arg Glu Ala Ser Asp Ala Lys Asn Glu
1               5                   10                  15

<210> SEQ ID NO 12
<211> LENGTH: 16
<212> TYPE: PRT
<213> ORGANISM: Homo sapiens

<400> SEQUENCE: 12

Ala Glu Glu Asp Arg Arg Lys Lys Glu Arg Val Glu Ala Val Asn Met
1               5                   10                  15

<210> SEQ ID NO 13
<211> LENGTH: 22
<212> TYPE: PRT
<213> ORGANISM: Chlamydia pneumoniae

<400> SEQUENCE: 13

Lys Lys His Ser Phe Ser Thr Lys Pro Pro Ser Asn Asn Gly Ser Ser
1               5                   10                  15
Glu Asp His Ile Glu Glu
            20

<210> SEQ ID NO 14
<211> LENGTH: 14
<212> TYPE: PRT
<213> ORGANISM: Chlamydia pneumoniae

<400> SEQUENCE: 14

Tyr Thr Val Thr Ser Gly Ser Lys Gly Asp Ala Val Phe Glu
 1               5                  10

<210> SEQ ID NO 15
<211> LENGTH: 11
<212> TYPE: PRT
<213> ORGANISM: Chlamydia pneumoniae

<400> SEQUENCE: 15

Thr Ser Ser Glu Gly Thr Arg Thr Thr Pro Ser
 1               5                  10

<210> SEQ ID NO 16
<211> LENGTH: 8
<212> TYPE: PRT
<213> ORGANISM: Chlamydia pneumoniae

<400> SEQUENCE: 16

Ser Glu His Lys Lys Ser Ser Lys
 1               5

<210> SEQ ID NO 17
<211> LENGTH: 14
<212> TYPE: PRT
<213> ORGANISM: Chlamydia pneumoniae

<400> SEQUENCE: 17

Lys Asp Val Ala Ser Gly Lys Glu Gln Lys Ile Arg Ile Glu
 1               5                  10

<210> SEQ ID NO 18
<211> LENGTH: 16
<212> TYPE: PRT
<213> ORGANISM: Chlamydia pneumoniae

<400> SEQUENCE: 18

Glu Arg Asn Thr Thr Ile Pro Thr Gln Lys Lys Gln Ile Phe Ser Thr
 1               5                  10                  15

<210> SEQ ID NO 19
<211> LENGTH: 16
<212> TYPE: PRT
<213> ORGANISM: Chlamydia pneumoniae

<400> SEQUENCE: 19

Tyr Phe Asn Asp Ser Gln Arg Ala Ser Ser Thr Lys Asp Ala Gly Arg
 1               5                  10                  15

<210> SEQ ID NO 20
<211> LENGTH: 15
<212> TYPE: PRT
<213> ORGANISM: Chlamydia pneumoniae

<400> SEQUENCE: 20

Glu Glu Phe Lys Lys Gln Glu Gly Ile Asp Leu Ser Lys Asp Asn
 1               5                  10                  15

<210> SEQ ID NO 21
<211> LENGTH: 12
<212> TYPE: PRT
<213> ORGANISM: Chlamydia pneumoniae

<400> SEQUENCE: 21

```
Asn Ala Lys Gly Gly Pro Asn Ile Asn Thr Glu Asp
 1               5                  10
```

<210> SEQ ID NO 22
<211> LENGTH: 16
<212> TYPE: PRT
<213> ORGANISM: Chlamydia pneumoniae

<400> SEQUENCE: 22

```
Gly Glu Arg Pro Met Ala Lys Asp Asn Lys Glu Ile Gly Arg Phe Asp
 1               5                  10                  15
```

<210> SEQ ID NO 23
<211> LENGTH: 14
<212> TYPE: PRT
<213> ORGANISM: Chlamydia pneumoniae

<400> SEQUENCE: 23

```
Thr Glu Ile Glu Met Lys Glu Lys Lys Asp Arg Val Asp Asp
 1               5                  10
```

<210> SEQ ID NO 24
<211> LENGTH: 14
<212> TYPE: PRT
<213> ORGANISM: Homo sapiens

<400> SEQUENCE: 24

```
Ser Asp Val Glu Val Asn Glu Lys Lys Asp Arg Val Thr Asp
 1               5                  10
```

<210> SEQ ID NO 25
<211> LENGTH: 11
<212> TYPE: PRT
<213> ORGANISM: Chlamydia pneumoniae

<400> SEQUENCE: 25

```
Glu Asp Ser Thr Ser Asp Tyr Asp Lys Glu Lys
 1               5                  10
```

<210> SEQ ID NO 26
<211> LENGTH: 11
<212> TYPE: PRT
<213> ORGANISM: Homo sapiens

<400> SEQUENCE: 26

```
Asp Val Thr Thr Ser Glu Tyr Glu Lys Glu Lys
 1               5                  10
```

<210> SEQ ID NO 27
<211> LENGTH: 7
<212> TYPE: PRT
<213> ORGANISM: Chlamydia pneumoniae

<400> SEQUENCE: 27

```
Asp Asp Lys Ser Ser Ser Ala
 1               5
```

<210> SEQ ID NO 28
<211> LENGTH: 15
<212> TYPE: PRT
<213> ORGANISM: Chlamydia pneumoniae

<400> SEQUENCE: 28

```
Lys Lys Gln Ile Glu Asp Ser Thr Ser Asp Tyr Val Ser Glu Glu
 1               5                  10                  15
```

<210> SEQ ID NO 29
<211> LENGTH: 12
<212> TYPE: PRT
<213> ORGANISM: Chlamydia pneumoniae

<400> SEQUENCE: 29

Ser Ser Tyr Phe Ser Thr Asn Pro Glu Thr Gln Glu
1               5                   10

<210> SEQ ID NO 30
<211> LENGTH: 16
<212> TYPE: PRT
<213> ORGANISM: Chlamydia pneumoniae

<400> SEQUENCE: 30

Glu Lys Val Gly Lys Asn Gly Ser Ile Thr Val Glu Glu Ala Asp Lys
1               5                   10                  15

<210> SEQ ID NO 31
<211> LENGTH: 15
<212> TYPE: PRT
<213> ORGANISM: Chlamydia pneumoniae

<400> SEQUENCE: 31

Ser Lys Thr Ala Asp Lys Ala Gly Asp Gly Thr Thr Thr Ala Thr
1               5                   10                  15

<210> SEQ ID NO 32
<211> LENGTH: 10
<212> TYPE: PRT
<213> ORGANISM: Chlamydia pneumoniae

<400> SEQUENCE: 32

Lys Arg Glu Glu Glu Glu Ala Thr Ala Arg
1               5                   10

<210> SEQ ID NO 33
<211> LENGTH: 10
<212> TYPE: PRT
<213> ORGANISM: Mouse

<400> SEQUENCE: 33

Glu Arg Ser Ala Ala Glu Thr Val Thr Lys
1               5                   10

<210> SEQ ID NO 34
<211> LENGTH: 11
<212> TYPE: PRT
<213> ORGANISM: Chlamydia pneumoniae

<400> SEQUENCE: 34

Asp Thr Ala Lys Lys Lys Gln Asp Arg Ala Glu
1               5                   10

<210> SEQ ID NO 35
<211> LENGTH: 11
<212> TYPE: PRT
<213> ORGANISM: Mouse

<400> SEQUENCE: 35

Glu Lys Ser Gln Gly Lys Val Leu Gln Ala Thr
1               5                   10

```
<210> SEQ ID NO 36
<211> LENGTH: 10
<212> TYPE: PRT
<213> ORGANISM: Chlamydia pneumoniae

<400> SEQUENCE: 36

Gly Thr Gly Lys Arg Thr Asp Asp Gly Thr
1               5                   10

<210> SEQ ID NO 37
<211> LENGTH: 10
<212> TYPE: PRT
<213> ORGANISM: Mouse

<400> SEQUENCE: 37

Gly Ser Gly Gly Lys Gly Lys Ser Gly Glu
1               5                   10

<210> SEQ ID NO 38
<211> LENGTH: 25
<212> TYPE: PRT
<213> ORGANISM: Chlamydia pneumoniae

<400> SEQUENCE: 38

Arg Arg Asn Lys Gln Pro Val Glu Gln Lys Ser Arg Gly Ala Phe Cys
1               5                   10                  15

Asp Lys Glu Phe Tyr Pro Cys Glu Glu
            20                  25

<210> SEQ ID NO 39
<211> LENGTH: 19
<212> TYPE: PRT
<213> ORGANISM: Chlamydia pneumoniae

<400> SEQUENCE: 39

Asp Met Arg Pro Gly Asp Lys Lys Val Phe Thr Val Glu Phe Cys Pro
1               5                   10                  15

Gln Arg Arg

<210> SEQ ID NO 40
<211> LENGTH: 19
<212> TYPE: PRT
<213> ORGANISM: Chlamydia pneumoniae

<400> SEQUENCE: 40

Ser Ser Asp Pro Glu Thr Thr Pro Thr Ser Asp Gly Lys Val Trp Lys
1               5                   10                  15

Ile Asp Arg

<210> SEQ ID NO 41
<211> LENGTH: 20
<212> TYPE: PRT
<213> ORGANISM: Chlamydia pneumoniae

<400> SEQUENCE: 41

Thr Ser Glu Ser Asn Cys Gly Thr Cys Thr Ser Cys Ala Glu Thr Thr
1               5                   10                  15

Thr His Trp Lys
            20

<210> SEQ ID NO 42
<211> LENGTH: 11
<212> TYPE: PRT
```

```
<213> ORGANISM: Chlamydia pneumoniae

<400> SEQUENCE: 42

Lys Leu Gly Ser Lys Glu Ser Val Glu Phe Ser
 1               5                  10

<210> SEQ ID NO 43
<211> LENGTH: 16
<212> TYPE: PRT
<213> ORGANISM: Chlamydia pneumoniae

<400> SEQUENCE: 43

Thr Val Tyr Arg Ile Cys Val Thr Asn Arg Gly Ser Ala Glu Asp Thr
 1               5                  10                  15

<210> SEQ ID NO 44
<211> LENGTH: 11
<212> TYPE: PRT
<213> ORGANISM: Chlamydia pneumoniae

<400> SEQUENCE: 44

Glu Tyr Ser Ile Ser Val Ser Asn Pro Gly Asp
 1               5                  10

<210> SEQ ID NO 45
<211> LENGTH: 100
<212> TYPE: PRT
<213> ORGANISM: Chlamydia trachomatis

<400> SEQUENCE: 45

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Gln Thr Asp Val Asn Lys
65                  70                  75                  80

Glu Phe Gln Met Gly Ala Lys Pro Thr Thr Ala Thr Gly Asn Ala Ala
                85                  90                  95

Ala Pro Ser Thr
            100

<210> SEQ ID NO 46
<211> LENGTH: 100
<212> TYPE: PRT
<213> ORGANISM: Chlamydia trachomatis

<400> SEQUENCE: 46

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Ile Met Gly Tyr
        50                  55                  60

Tyr Gly Asp Phe Val Phe Asp Arg Val Leu Lys Thr Asp Val Asn Lys
```

```
            65                  70                  75                  80
Glu Phe Gln Met Gly Ala Lys Pro Thr Thr Thr Gly Asn Ala Ala
                    85                  90                  95

Ala Pro Ser Thr
            100

<210> SEQ ID NO 47
<211> LENGTH: 100
<212> TYPE: PRT
<213> ORGANISM: Chlamydia trachomatis

<400> SEQUENCE: 47

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Glu Thr Asp Val Asn Lys
 65                 70                  75                  80

Glu Phe His Met Gly Ala Lys Pro Thr Thr Asp Thr Gly Asn Ser Ala
                    85                  90                  95

Ala Pro Leu Thr
            100

<210> SEQ ID NO 48
<211> LENGTH: 100
<212> TYPE: PRT
<213> ORGANISM: Chlamydia trachomatis

<400> SEQUENCE: 48

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Ile Met Gly Tyr
        50                  55                  60

Tyr Gly Asp Phe Val Phe Asp Arg Val Leu Lys Thr Asp Val Asn Lys
 65                 70                  75                  80

Glu Phe His Met Gly Asp Lys Pro Thr Ser Thr Gly Asn Ala Thr
                    85                  90                  95

Ala Pro Thr Thr
            100

<210> SEQ ID NO 49
<211> LENGTH: 100
<212> TYPE: PRT
<213> ORGANISM: Chlamydia trachomatis

<400> SEQUENCE: 49

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                20                  25                  30
```

```
Leu Met Ile Asp Gly Ile Leu Trp Glu Gly Phe Gly Gly Asp Pro Cys
         35                  40                  45

Asp Pro Cys Thr Thr Trp Cys Asp Ala Ile Ser Met Ile Met Gly Tyr
     50                  55                  60

Tyr Gly Asp Phe Val Phe Asp Arg Val Leu Lys Thr Asp Val Asn Lys
 65                  70                  75                  80

Glu Phe His Met Gly Asp Lys Pro Thr Ala Thr Thr Gly Asn Ala Ala
                 85                  90                  95

Ala Pro Ser Thr
            100

<210> SEQ ID NO 50
<211> LENGTH: 101
<212> TYPE: PRT
<213> ORGANISM: Chlamydia trachomatis

<400> SEQUENCE: 50

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
             20                  25                  30

Leu Met Ile Asp Gly Ile Leu Trp Glu Gly Phe Gly Gly Asp Pro Cys
         35                  40                  45

Asp Pro Cys Thr Thr Trp Cys Asp Ala Ile Ser Met Ile Met Gly Tyr
     50                  55                  60

Tyr Gly Asp Phe Val Phe Asp Arg Val Leu Lys Thr Asp Val Asn Lys
 65                  70                  75                  80

Glu Phe Lys Met Gly Glu Ala Leu Ala Gly Ser Thr Gly Asn Thr Thr
                 85                  90                  95

Ser Thr Leu Ser Lys
            100

<210> SEQ ID NO 51
<211> LENGTH: 103
<212> TYPE: PRT
<213> ORGANISM: Chlamydia trachomatis

<400> SEQUENCE: 51

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
             20                  25                  30

Leu Met Ile Asp Gly Ile Leu Trp Glu Gly Phe Gly Gly Asp Pro Cys
         35                  40                  45

Asp Pro Cys Thr Thr Trp Cys Asp Ala Ile Ser Met Val Met Gly Tyr
     50                  55                  60

Tyr Gly Asp Phe Val Phe Asp Arg Val Leu Lys Thr Asp Val Asn Lys
 65                  70                  75                  80

Glu Phe Gln Met Gly Ala Ala Pro Thr Thr Ser Asp Val Ala Ala Gly
                 85                  90                  95

Leu Gln Asn Asp Pro Thr Ile
            100

<210> SEQ ID NO 52
<211> LENGTH: 102
<212> TYPE: PRT
<213> ORGANISM: Chlamydia trachomatis
```

```
<400> SEQUENCE: 52

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Arg Asp Val Ala Gly Leu
                85                  90                  95

Glu Lys Asp Pro Val Val
            100

<210> SEQ ID NO 53
<211> LENGTH: 97
<212> TYPE: PRT
<213> ORGANISM: Chlamydia trachomatis

<400> SEQUENCE: 53

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Ala Pro Cys Thr Thr Trp Cys Asp Ala Ile Ser Met Val Met Gly Tyr
        50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Asn Asp Ala Ala Pro Lys
                85                  90                  95

Thr

<210> SEQ ID NO 54
<211> LENGTH: 102
<212> TYPE: PRT
<213> ORGANISM: Chlamydia trachomatis

<400> SEQUENCE: 54

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Val Met Gly Tyr
        50                  55                  60

Tyr Gly Asp Phe Val Phe Asp Arg Val Leu Lys Thr Asp Val Asn Lys
65                  70                  75                  80

Glu Phe Gln Met Gly Ala Glu Pro Thr Thr Ser Asp Thr Ala Gly Leu
                85                  90                  95

Ser Asn Asp Pro Thr Thr
```

SEQ ID NO 55

LENGTH: 100
TYPE: PRT
<213> ORGANISM: Chlamydia trachomatis

<400> SEQUENCE: 55

Met Lys Lys Leu Leu Lys Ser Val Ala Val Phe Val Ala Gly Ser Ser
1               5                   10                  15

Ala Ser Ser Leu His Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Leu
    50                  55                  60

Tyr Leu Asp Phe Val Phe Asp Arg Val Leu Lys Thr Asp Val Asn Lys
65                  70                  75                  80

Gln Phe Glu Met Gly Ala Ala Pro Thr Gly Asp Ala Asp Leu Thr Thr
                85                  90                  95

Ala Pro Thr Pro
            100

<210> SEQ ID NO 56
<211> LENGTH: 99
<212> TYPE: PRT
<213> ORGANISM: Chlamydia pneumoniae

<400> SEQUENCE: 56

Met Lys Lys Leu Leu Lys Ala Val Leu Ala Phe Ala Phe Ala Gly Ser
1               5                   10                  15

Val Gly Ser Leu Gln Ala Leu Pro Val Gly Asn Pro Ala Ser Asp Ser
            20                  25                  30

Leu Leu Ile Asp Gly Thr Ile Trp Glu Gly Ala Ala Gly Asp Pro Cys
        35                  40                  45

Asp Pro Ala Thr Thr Trp Cys Asp Ala Ile Ser Leu Arg Ala Gly Phe
    50                  55                  60

Tyr Gly Asp Phe Val Tyr Asp Ile Val Leu Lys Val Asp Ala Pro Lys
65                  70                  75                  80

Thr Phe Ser Met Gly Ala Lys Pro Thr Thr Thr Gly Asn Gly Ser Ala
                85                  90                  95

Ala Ala Asn

<210> SEQ ID NO 57
<211> LENGTH: 100
<212> TYPE: PRT
<213> ORGANISM: Chlamydia trachomatis

<400> SEQUENCE: 57

Cys Thr Ala Arg Glu Asn Pro Ala Tyr Gly Arg His Met Gln Asp Ala
1               5                   10                  15

Glu Met Phe Thr Asn Ala Ala Tyr Met Ala Leu Ile Asn Trp Asp Arg
            20                  25                  30

Phe Asp Val Phe Cys Thr Leu Gly Ala Thr Ser Gly Tyr Leu Lys Gly
        35                  40                  45

Asn Ser Ala Ser Phe Asn Leu Val Gly Leu Phe Gly Asp Asn Glu Asn
    50                  55                  60

His Ala Thr Val Ser Asp Ser Lys Leu Val Pro Asn Met Ser Leu Asp
65                  70                  75                  80

Gln Ser Val Val Glu Leu Tyr Thr Asp Thr Thr Phe Ala Trp Ser Ala
                85                  90                  95

Gly Ala Arg Ala
            100

<210> SEQ ID NO 58
<211> LENGTH: 65
<212> TYPE: PRT
<213> ORGANISM: Chlamydia trachomatis

<400> SEQUENCE: 58

Leu Thr Ala Arg Glu Asn Pro Ala Tyr Gly Arg His Met Gln Asp Ala
1               5                   10                  15

Glu Met Phe Thr Asn Cys Ala Tyr Met Ala Leu Ile Asn Trp Asp Arg
            20                  25                  30

Phe Asp Val Phe Cys Thr Leu Gly Ala Ser Ser Gly Tyr Leu Lys Gly
        35                  40                  45

Asn Ser Ala Ser Phe Asn Leu Val Gly Leu Phe Gly Asn Asn Glu Asn
    50                  55                  60

Gln
65

<210> SEQ ID NO 59
<211> LENGTH: 134
<212> TYPE: PRT
<213> ORGANISM: Chlamydia trachomatis

<400> SEQUENCE: 59

Cys Thr Ala Arg Glu Asn Pro Ala Tyr Gly Arg His Met Gln Asp Ala
1               5                   10                  15

Glu Met Phe Thr Asn Cys Ala Tyr Met Ala Leu Ile Asn Trp Asp Arg
            20                  25                  30

Phe Asp Val Phe Cys Thr Leu Gly Ala Thr Ser Gly Tyr Leu Lys Gly
        35                  40                  45

Asn Ser Ala Ser Phe Asn Leu Val Gly Leu Phe Gly Asp Asn Glu Asn
    50                  55                  60

Gln Lys Thr Val Lys Ala Glu Ser Val Pro Asn Met Ser Phe Asp Gln
65                  70                  75                  80

Ser Val Val Glu Leu Tyr Thr Asp Thr Thr Phe Ala Trp Ser Val Gly
                85                  90                  95

Ala Arg Ala Thr Lys Val Ser Asn Gly Thr Phe Val Pro Asn Met Ser
            100                 105                 110

Leu Asp Gln Ser Val Val Glu Leu Tyr Thr Asp Thr Ala Phe Ala Trp
        115                 120                 125

Ser Val Gly Ala Arg Ala
            130

<210> SEQ ID NO 60
<211> LENGTH: 99
<212> TYPE: PRT
<213> ORGANISM: Chlamydia trachomatis

<400> SEQUENCE: 60

Leu Thr Ala Arg Glu Asn Pro Ala Tyr Gly Arg His Met Gln Asp Ala
1               5                   10                  15

```
Glu Met Phe Thr Asn Cys Ala Tyr Met Ala Leu Ile Asn Trp Asp Arg
             20                  25                  30

Phe Asp Val Phe Cys Thr Leu Gly Ala Ser Ser Gly Tyr Leu Lys Gly
         35                  40                  45

Asn Ser Ala Ser Phe Asn Leu Val Gly Leu Phe Gly Asp Asn Glu Asn
     50                  55                  60

Gln Ser Thr Val Lys Thr Asn Ser Val Pro Asn Met Ser Leu Asp Gln
65                  70                  75                  80

Ser Val Val Glu Leu Tyr Thr Asp Thr Ala Phe Ser Trp Ser Val Gly
                 85                  90                  95

Ala Arg Ala

<210> SEQ ID NO 61
<211> LENGTH: 99
<212> TYPE: PRT
<213> ORGANISM: Chlamydia trachomatis

<400> SEQUENCE: 61

Cys Thr Ala Arg Glu Asn Pro Ala Tyr Gly Arg His Met Gln Asp Ala
1               5                  10                  15

Glu Met Phe Thr Asn Ala Ala Tyr Met Ala Leu Ile Asn Trp Asp Arg
             20                  25                  30

Phe Asp Val Phe Cys Thr Leu Gly Ala Thr Ser Gly Tyr Leu Lys Gly
         35                  40                  45

Asn Ser Ala Ser Phe Asn Leu Val Gly Leu Phe Gly Asp Asn Glu Asn
     50                  55                  60

Gln Ser Thr Val Lys Lys Asp Ala Val Pro Asn Met Ser Phe Asp Gln
65                  70                  75                  80

Ser Val Val Glu Leu Tyr Thr Asp Thr Phe Ala Trp Ser Val Gly
                 85                  90                  95

Ala Arg Ala

<210> SEQ ID NO 62
<211> LENGTH: 99
<212> TYPE: PRT
<213> ORGANISM: Chlamydia trachomatis

<400> SEQUENCE: 62

Leu Val Glu Arg Thr Asn Pro Ala Tyr Gly Lys His Met Gln Asp Ala
1               5                  10                  15

Glu Met Phe Thr Asn Cys Ala Tyr Thr Ala Leu Ile Asn Trp Asp Arg
             20                  25                  30

Phe Asp Val Phe Cys Thr Leu Gly Ala Thr Ser Gly Tyr Leu Lys Gly
         35                  40                  45

Asn Ser Ala Ser Phe Asn Leu Val Gly Leu Phe Gly Asp Gly Val Asn
     50                  55                  60

Ala Thr Lys Pro Ala Ala Asp Ser Ile Pro Asn Val Gln Leu Asn Gln
65                  70                  75                  80

Ser Val Val Glu Leu Tyr Thr Asp Thr Phe Ala Trp Ser Val Gly
                 85                  90                  95

Ala Arg Ala

<210> SEQ ID NO 63
<211> LENGTH: 100
<212> TYPE: PRT
<213> ORGANISM: Chlamydia trachomatis
```

```
<400> SEQUENCE: 63

Asn Val Ala Arg Pro Asn Pro Ala Tyr Gly Lys His Met Gln Asp Ala
1               5                   10                  15

Glu Met Phe Thr Asn Ala Ala Tyr Met Ala Leu Ile Asn Trp Asp Arg
            20                  25                  30

Phe Asp Val Phe Cys Thr Leu Gly Ala Thr Thr Gly Tyr Leu Lys Gly
        35                  40                  45

Asn Ser Ala Ser Phe Asn Leu Val Gly Leu Phe Gly Thr Lys Thr Gln
    50                  55                  60

Ser Ser Ser Phe Asn Thr Ala Lys Leu Ile Pro Asn Thr Ala Leu Asp
65                  70                  75                  80

Gln Ser Val Val Glu Leu Tyr Ile Asn Thr Thr Phe Ala Trp Ser Val
                85                  90                  95

Gly Ala Arg Ala
            100

<210> SEQ ID NO 64
<211> LENGTH: 100
<212> TYPE: PRT
<213> ORGANISM: Chlamydia trachomatis

<400> SEQUENCE: 64

Asn Val Ala Arg Pro Asn Pro Ala Tyr Gly Lys His Met Gln Asp Ala
1               5                   10                  15

Glu Met Phe Thr Asn Ala Ala Tyr Met Ala Leu Ile Asn Trp Asp Arg
            20                  25                  30

Phe Asp Val Phe Cys Thr Leu Gly Ala Thr Thr Gly Tyr Leu Lys Gly
        35                  40                  45

Asn Ser Ala Ser Phe Asn Leu Val Gly Leu Phe Gly Thr Lys Thr Gln
    50                  55                  60

Ser Ser Gly Phe Asp Thr Ala Asn Ile Val Pro Asn Thr Ala Leu Asn
65                  70                  75                  80

Gln Ala Val Val Glu Leu Tyr Thr Asp Thr Thr Phe Ala Trp Ser Val
                85                  90                  95

Gly Ala Arg Ala
            100

<210> SEQ ID NO 65
<211> LENGTH: 100
<212> TYPE: PRT
<213> ORGANISM: Chlamydia trachomatis

<400> SEQUENCE: 65

Asn Val Ala Arg Pro Asn Pro Ala Tyr Gly Lys His Met Gln Asp Ala
1               5                   10                  15

Glu Met Phe Thr Asn Ala Ala Tyr Met Ala Leu Ile Asn Trp Asp Arg
            20                  25                  30

Phe Asp Val Phe Cys Thr Leu Gly Ala Thr Thr Gly Tyr Leu Lys Gly
        35                  40                  45

Asn Ser Ala Ser Phe Asn Leu Val Gly Leu Phe Gly Thr Lys Thr Lys
    50                  55                  60

Ser Ser Asp Phe Asn Thr Ala Lys Leu Val Pro Asn Ile Ala Leu Asn
65                  70                  75                  80

Arg Ala Val Val Glu Leu Tyr Thr Asp Thr Thr Phe Ala Trp Ser Val
                85                  90                  95

Gly Ala Arg Ala
```

100

```
<210> SEQ ID NO 66
<211> LENGTH: 100
<212> TYPE: PRT
<213> ORGANISM: Chlamydia trachomatis

<400> SEQUENCE: 66
```

Asn Val Ala Arg Pro Asn Pro Ala Tyr Gly Lys His Met Gln Asp Ala
1               5                   10                  15

Glu Met Phe Thr Asn Ala Ala Tyr Met Ala Leu Ile Asn Trp Asp Arg
            20                  25                  30
Phe Asp Val Phe Cys Thr Leu Gly Ala Thr Thr Gly Tyr Leu Lys Gly
        35                  40                  45

Asn Ser Ala Ser Phe Asn Leu Val Gly Leu Phe Gly Thr Lys Thr Gln
    50                  55                  60

Ser Thr Asn Phe Asn Thr Ala Lys Leu Val Pro Asn Thr Ala Leu Asn
65                  70                  75                  80

Gln Ala Val Val Glu Leu Tyr Thr Asp Thr Thr Phe Ala Trp Ser Val
                85                  90                  95

Gly Ala Arg Ala
            100

```
<210> SEQ ID NO 67
<211> LENGTH: 96
<212> TYPE: PRT
<213> ORGANISM: Chlamydia trachomatis

<400> SEQUENCE: 67
```

Ala Ser Arg Glu Asn Pro Ala Tyr Gly Lys His Met Gln Asp Ala Glu
1               5                   10                  15

Met Phe Thr Asn Ala Ala Tyr Met Ala Leu Ile Asn Trp Asp Arg Phe
            20                  25                  30

Asp Val Phe Cys Thr Leu Gly Ala Thr Ser Gly Tyr Leu Lys Gly Asn
        35                  40                  45

Ser Ala Ala Phe Asn Leu Val Gly Leu Phe Gly Arg Asp Glu Thr Ala
    50                  55                  60

Val Ala Ala Asp Asp Ile Pro Asn Val Ser Leu Ser Gln Ala Val Val
65                  70                  75                  80

Glu Leu Tyr Thr Asp Thr Ala Phe Ala Trp Ser Val Gly Ala Arg Ala
                85                  90                  95

```
<210> SEQ ID NO 68
<211> LENGTH: 100
<212> TYPE: PRT
<213> ORGANISM: Chlamydia pneumoniae

<400> SEQUENCE: 68
```

Tyr Thr Thr Ala Val Asp Arg Pro Asn Pro Ala Tyr Asn Lys His Leu
1               5                   10                  15

His Asp Ala Glu Trp Phe Thr Asn Ala Gly Ile Phe Ala Leu Ile Asn
            20                  25                  30

Trp Asp Arg Phe Asp Val Phe Cys Thr Leu Gly Ala Ser Asn Gly Ile
        35                  40                  45

Arg Lys Gly Asn Ser Thr Ala Phe Asn Leu Val Gly Leu Phe Gly Val
    50                  55                  60

Lys Gly Thr Thr Val Asn Ala Asn Glu Leu Pro Asn Val Ser Leu Ser
65                  70                  75                  80

```
Asn Gly Val Val Glu Leu Tyr Thr Asp Thr Ser Phe Ser Trp Ser Val
                85                  90                  95
Gly Ala Arg Ala
            100

<210> SEQ ID NO 69
<211> LENGTH: 100
<212> TYPE: PRT
<213> ORGANISM: Chlamydia trachomatis

<400> SEQUENCE: 69

Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asn Ala
                20                  25                  30

Ala Glu Phe Thr Ile Asn Lys Pro Lys Gly Tyr Val Gly Gln Glu Phe
            35                  40                  45

Pro Leu Asp Leu Lys Ala Gly Thr Asp Gly Val Thr Gly Thr Lys Asp
        50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 70
<211> LENGTH: 100
<212> TYPE: PRT
<213> ORGANISM: Chlamydia trachomatis

<400> SEQUENCE: 70

Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asn Ala
                20                  25                  30

Ala Glu Phe Thr Ile Asn Lys Pro Lys Gly Tyr Val Gly Lys Glu Leu
            35                  40                  45

Pro Leu Asp Leu Thr Ala Gly Thr Asp Ala Ala Thr Gly Thr Lys Asp
        50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 71
<211> LENGTH: 100
<212> TYPE: PRT
<213> ORGANISM: Chlamydia trachomatis

<400> SEQUENCE: 71

Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asn Ala
                20                  25                  30

Ala Glu Phe Thr Ile Asn Lys Pro Lys Gly Tyr Val Gly Lys Glu Phe
```

-continued

```
                 35                  40                  45
Pro Leu Asp Leu Thr Ala Gly Thr Asp Ala Ala Thr Gly Thr Lys Asp
     50                  55                  60
Ala Ser Ile Asp Tyr His Glu Trp Gln Ala Ser Leu Ala Leu Ser Tyr
 65                  70                  75                  80
Arg Leu Asn Met Phe Thr Pro Tyr Ile Gly Val Lys Trp Ser Arg Ala
                 85                  90                  95
Ser Phe Asp Ala
            100

<210> SEQ ID NO 72
<211> LENGTH: 100
<212> TYPE: PRT
<213> ORGANISM: Chlamydia trachomatis

<400> SEQUENCE: 72

Ala Leu Trp Glu Cys Gly Cys Ala Thr Leu Gly Ala Ser Phe Gln Tyr
 1               5                  10                  15
Ala Gln Ser Lys Pro Lys Val Glu Glu Leu Asn Val Leu Cys Asn Ala
                 20                  25                  30
Ala Glu Phe Thr Ile Asn Lys Pro Lys Gly Tyr Val Gly Gln Glu Phe
             35                  40                  45
Pro Leu Ala Leu Ile Ala Gly Thr Asp Ala Ala Thr Gly Thr Lys Asp
     50                  55                  60
Ala Ser Ile Asp Tyr His Glu Trp Gln Ala Ser Leu Ala Leu Ser Tyr
 65                  70                  75                  80
Arg Leu Asn Met Phe Thr Pro Tyr Ile Gly Val Lys Trp Ser Arg Ala
                 85                  90                  95
Ser Phe Asp Ala
            100

<210> SEQ ID NO 73
<211> LENGTH: 100
<212> TYPE: PRT
<213> ORGANISM: Chlamydia trachomatis

<400> SEQUENCE: 73

Ala Leu Trp Glu Cys Gly Cys Ala Thr Leu Gly Ala Ser Phe Gln Tyr
 1               5                  10                  15
Ala Gln Ser Lys Pro Lys Val Glu Glu Leu Asn Val Leu Cys Asn Ala
                 20                  25                  30
Ala Glu Phe Thr Ile Asn Lys Pro Lys Gly Tyr Val Gly Lys Glu Phe
             35                  40                  45
Pro Leu Asp Leu Thr Ala Gly Thr Asp Ala Ala Thr Gly Thr Lys Asp
     50                  55                  60
Ala Ser Ile Asp Tyr His Glu Trp Gln Ala Ser Leu Ala Leu Ser Tyr
 65                  70                  75                  80
Arg Leu Asn Met Phe Thr Pro Tyr Ile Gly Val Lys Trp Ser Arg Ala
                 85                  90                  95
Ser Phe Asp Ala
            100

<210> SEQ ID NO 74
<211> LENGTH: 100
<212> TYPE: PRT
<213> ORGANISM: Chlamydia trachomatis

<400> SEQUENCE: 74
```

```
Ala Leu Trp Glu Cys Gly Cys Ala Thr Leu Gly Ala Ser Phe Gln Tyr
  1               5                  10                  15

Ala Gln Ser Lys Pro Lys Ile Glu Glu Leu Asn Val Leu Cys Asn Ala
              20                  25                  30

Ala Glu Phe Thr Ile Asn Lys Pro Lys Gly Tyr Val Gly Lys Glu Phe
          35                  40                  45

Pro Leu Asp Leu Thr Ala Gly Thr Asp Ala Ala Thr Gly Thr Lys Asp
     50                  55                  60

Ala Ser Ile Asp Tyr His Glu Trp Gln Ala Ser Leu Ser Leu Ser Tyr
 65                  70                  75                  80

Arg Leu Asn Met Phe Thr Pro Tyr Ile Gly Val Lys Trp Ser Arg Ala
                 85                  90                  95

Ser Phe Asp Ser
            100

<210> SEQ ID NO 75
<211> LENGTH: 100
<212> TYPE: PRT
<213> ORGANISM: Chlamydia trachomatis

<400> SEQUENCE: 75

Ala Leu Trp Glu Cys Gly Cys Ala Thr Leu Gly Ala Ser Phe Gln Tyr
  1               5                  10                  15

Ala Gln Ser Lys Pro Lys Val Glu Glu Leu Asn Val Leu Cys Asn Ala
              20                  25                  30

Ser Glu Phe Thr Ile Asn Lys Pro Lys Gly Tyr Val Gly Ala Glu Phe
          35                  40                  45

Pro Leu Asn Ile Thr Ala Gly Thr Glu Ala Ala Thr Gly Thr Lys Asp
     50                  55                  60

Ala Ser Ile Asp Tyr His Glu Trp Gln Ala Ser Leu Ala Leu Ser Tyr
 65                  70                  75                  80

Arg Leu Asn Met Phe Thr Pro Tyr Ile Gly Val Lys Trp Ser Arg Val
                 85                  90                  95

Ser Phe Asp Ala
            100

<210> SEQ ID NO 76
<211> LENGTH: 100
<212> TYPE: PRT
<213> ORGANISM: Chlamydia trachomatis

<400> SEQUENCE: 76

Ala Leu Trp Glu Cys Gly Cys Ala Thr Leu Gly Ala Ser Phe Gln Tyr
  1               5                  10                  15

Ala Gln Ser Lys Pro Lys Val Glu Glu Leu Asn Val Leu Cys Asn Ala
              20                  25                  30

Ser Glu Phe Thr Ile Asn Lys Pro Lys Gly Tyr Val Gly Ala Glu Phe
          35                  40                  45

Pro Leu Asp Ile Thr Ala Gly Thr Glu Ala Ala Thr Gly Thr Lys Asp
     50                  55                  60

Ala Ser Ile Asp Tyr His Glu Trp Gln Ala Ser Leu Ala Leu Ser Tyr
 65                  70                  75                  80

Arg Leu Asn Met Phe Thr Pro Tyr Ile Gly Val Lys Trp Ser Arg Val
                 85                  90                  95

Ser Phe Asp Ala
            100
```

<210> SEQ ID NO 77
<211> LENGTH: 100
<212> TYPE: PRT
<213> ORGANISM: Chlamydia trachomatis

<400> SEQUENCE: 77

```
Ala Leu Trp Glu Cys Gly Cys Ala Thr Leu Gly Ala Ser Phe Gln Tyr
  1               5                  10                  15

Ala Gln Ser Lys Pro Lys Val Glu Glu Leu Asn Val Leu Cys Asn Ala
             20                  25                  30

Ser Glu Phe Thr Ile Asn Lys Pro Lys Gly Tyr Val Gly Ala Glu Phe
         35                  40                  45

Pro Leu Asp Ile Thr Ala Gly Thr Glu Ala Ala Thr Gly Thr Lys Asp
     50                  55                  60

Ala Ser Ile Asp Tyr His Glu Trp Gln Ala Ser Leu Ala Leu Ser Tyr
 65                  70                  75                  80

Arg Leu Asn Met Phe Thr Pro Tyr Ile Gly Val Lys Trp Ser Arg Val
                 85                  90                  95

Ser Phe Asp Ala
            100
```

<210> SEQ ID NO 78
<211> LENGTH: 100
<212> TYPE: PRT
<213> ORGANISM: Chlamydia trachomatis

<400> SEQUENCE: 78

```
Ala Leu Trp Glu Cys Gly Cys Ala Thr Leu Gly Ala Ser Phe Gln Tyr
  1               5                  10                  15

Ala Gln Ser Lys Pro Lys Val Glu Glu Leu Asn Val Leu Cys Asp Ala
             20                  25                  30

Ser Glu Phe Thr Ile Asn Lys Pro Lys Gly Tyr Val Gly Ala Glu Phe
         35                  40                  45

Pro Leu Asp Ile Thr Ala Gly Thr Glu Ala Ala Thr Gly Thr Lys Asp
     50                  55                  60

Ala Ser Ile Asp Tyr His Glu Trp Gln Ala Ser Leu Ala Leu Ser Tyr
 65                  70                  75                  80

Arg Leu Asn Met Phe Thr Pro Tyr Ile Gly Val Lys Trp Ser Arg Val
                 85                  90                  95

Ser Phe Asp Ala
            100
```

<210> SEQ ID NO 79
<211> LENGTH: 100
<212> TYPE: PRT
<213> ORGANISM: Chlamydia trachomatis

<400> SEQUENCE: 79

```
Ala Leu Trp Glu Cys Gly Cys Ala Thr Leu Gly Ala Ser Phe Gln Tyr
  1               5                  10                  15

Ala Gln Ser Lys Pro Lys Val Glu Glu Leu Asn Val Leu Cys Asn Ala
             20                  25                  30

Ala Glu Phe Thr Ile Asn Lys Pro Lys Gly Tyr Val Gly Gln Glu Phe
         35                  40                  45

Pro Leu Asn Ile Lys Ala Gly Val Ser Ala Thr Asp Thr Lys Asp
     50                  55                  60
```

-continued

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 80
<211> LENGTH: 100
<212> TYPE: PRT
<213> ORGANISM: Chlamydia pneumoniae

<400> SEQUENCE: 80

Gly Leu Trp Glu Cys Gly Cys Ala Thr Leu Gly Glu Ser Phe Gln Tyr
1               5                   10                  15

Ala Gln Ser Lys Pro Lys Val Glu Leu Asn Val Ile Cys Asn Val
            20                  25                  30

Ser Gln Phe Ser Val Asn Lys Pro Lys Gly Tyr Lys Gly Val Ala Phe
            35                  40                  45

Pro Leu Pro Thr Asp Ala Gly Val Ala Thr Ala Thr Gly Thr Lys Ser
    50                  55                  60

Ala Thr Ile Asn Tyr His Glu Trp Gln Val Gly Ala Ser Leu Ser Tyr
65                  70                  75                  80

Arg Leu Asn Ser Leu Val Pro Tyr Ile Gly Val Gln Trp Ser Arg Ala
                85                  90                  95

Thr Phe Asp Ala
            100

<210> SEQ ID NO 81
<211> LENGTH: 94
<212> TYPE: PRT
<213> ORGANISM: Chlamydia trachomatis

<400> SEQUENCE: 81

Asp Thr Ile Arg Ile Ala Gln Pro Lys Ser Ala Thr Thr Val Phe Asp
1               5                   10                  15

Val Thr Thr Leu Asn Pro Thr Ile Ala Gly Ala Gly Asp Val Lys Ala
                20                  25                  30

Ser Ala Glu Gly Gln Leu Gly Asp Thr Met Gln Ile Val Ser Leu Gln
            35                  40                  45

Leu Asn Lys Met Lys Ser Arg Lys Ser Cys Gly Ile Ala Val Gly Thr
        50                  55                  60

Thr Ile Val Asp Ala Asp Lys Tyr Ala Val Thr Val Glu Thr Arg Leu
65                  70                  75                  80

Ile Asp Glu Arg Ala Ala His Val Asn Ala Gln Phe Arg Phe
                85                  90

<210> SEQ ID NO 82
<211> LENGTH: 92
<212> TYPE: PRT
<213> ORGANISM: Chlamydia trachomatis

<400> SEQUENCE: 82

Asp Thr Ile Arg Ile Ala Gln Pro Lys Ser Ala Glu Thr Ile Phe Asp
1               5                   10                  15

Val Thr Thr Leu Asn Pro Thr Ile Ala Gly Ala Gly Asp Val Lys Thr
                20                  25                  30

Ser Ala Glu Gly Gln Leu Gly Asp Thr Met Gln Ile Val Ser Leu Gln

```
                35                  40                  45
Leu Asn Met Lys Ser Arg Lys Cys Gly Ile Ala Val Gly Thr Thr Ile
         50                  55                  60
Val Asp Ala Asp Lys Tyr Ala Ile Thr Val Glu Thr Arg Leu Ile Asp
 65                  70                  75                  80
Glu Arg Ala Ala His Val Asn Ala Gln Phe Arg Phe
                 85                  90
```

<210> SEQ ID NO 83
<211> LENGTH: 94
<212> TYPE: PRT
<213> ORGANISM: Chlamydia trachomatis

<400> SEQUENCE: 83

```
Asp Thr Ile Arg Ile Ala Gln Pro Lys Ser Thr Ala Ile Phe Asp
  1               5                  10                  15
Thr Thr Thr Leu Asn Pro Thr Ile Ala Gly Ala Gly Asp Val Lys Thr
                 20                  25                  30
Gly Thr Glu Gly Gln Leu Gly Asp Thr Met Gln Ile Val Ser Leu Gln
             35                  40                  45
Leu Asn Lys Met Lys Ser Arg Lys Ser Cys Gly Ile Ala Val Gly Thr
         50                  55                  60
Thr Ile Val Asp Ala Asp Lys Tyr Ala Val Thr Val Glu Thr Arg Leu
 65                  70                  75                  80
Ile Asp Glu Arg Ala Ala His Val Asn Ala Gln Phe Arg Phe
                 85                  90
```

<210> SEQ ID NO 84
<211> LENGTH: 94
<212> TYPE: PRT
<213> ORGANISM: Chlamydia trachomatis

<400> SEQUENCE: 84

```
Asp Thr Ile Arg Ile Ala Gln Pro Lys Ser Thr Ala Ile Phe Asp
  1               5                  10                  15
Thr Thr Thr Leu Asn Pro Thr Ile Ala Gly Ala Gly Asp Val Lys Ala
                 20                  25                  30
Ser Ala Glu Gly Gln Leu Gly Asp Thr Met Gln Ile Val Ser Leu Gln
             35                  40                  45
Leu Asn Lys Met Lys Ser Arg Lys Ser Cys Gly Ile Ala Val Gly Thr
         50                  55                  60
Thr Ile Val Asp Ala Asp Lys Tyr Ala Val Thr Val Glu Thr Arg Leu
 65                  70                  75                  80
Ile Asp Glu Arg Ala Ala His Val Asn Ala Gln Phe Arg Phe
                 85                  90
```

<210> SEQ ID NO 85
<211> LENGTH: 94
<212> TYPE: PRT
<213> ORGANISM: Chlamydia trachomatis

<400> SEQUENCE: 85

```
Asp Thr Ile Arg Ile Ala Gln Pro Lys Leu Ala Thr Ala Ile Phe Asp
  1               5                  10                  15
Thr Thr Thr Leu Asn Pro Thr Ile Ala Gly Ala Gly Asp Glu Lys Ala
                 20                  25                  30
Asn Ala Glu Gly Gln Leu Gly Asp Thr Met Gln Ile Val Ser Leu Gln
             35                  40                  45
```

```
Leu Asn Lys Met Lys Ser Arg Lys Ser Cys Gly Ile Ala Val Gly Thr
        50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                85                  90
```

<210> SEQ ID NO 86
<211> LENGTH: 95
<212> TYPE: PRT
<213> ORGANISM: Chlamydia trachomatis

<400> SEQUENCE: 86

```
Asp Thr Ile Arg Ile Ala Gln Pro Arg Leu Val Thr Pro Val Val Asp
  1               5                  10                  15

Ile Thr Thr Leu Asn Pro Thr Ile Ala Gly Ala Cys Asp Ser Lys Ala
                20                  25                  30

Gly Asn Thr Glu Gly Gln Ile Ser Asp Thr Met Gln Ile Val Ser Leu
            35                  40                  45

Gln Leu Asn Lys Met Lys Ser Arg Lys Ser Cys Gly Ile Ala Val Gly
        50                  55                  60

Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg Phe
                85                  90                  95
```

<210> SEQ ID NO 87
<211> LENGTH: 95
<212> TYPE: PRT
<213> ORGANISM: Chlamydia trachomatis

<400> SEQUENCE: 87

```
Asp Thr Ile Arg Ile Ala Gln Pro Lys Leu Ala Glu Ala Ile Leu Asp
  1               5                  10                  15

Val Thr Thr Leu Asn Arg Thr Thr Ala Gly Lys Gly Ser Val Val Ser
                20                  25                  30

Ala Gly Thr Asp Asn Glu Leu Ala Asp Thr Met Gln Ile Val Ser Leu
            35                  40                  45

Gln Leu Asn Lys Met Lys Ser Arg Lys Ser Cys Gly Ile Ala Val Gly
        50                  55                  60

Thr Thr Ile Val Asp Ala Asp Lys Tyr Ala Val Thr Val Glu Ala Arg
 65                  70                  75                  80

Leu Ile Asp Glu Arg Ala Ala His Val Asn Ala Gln Phe Arg Phe
                85                  90                  95
```

<210> SEQ ID NO 88
<211> LENGTH: 94
<212> TYPE: PRT
<213> ORGANISM: Chlamydia trachomatis

<400> SEQUENCE: 88

```
Asp Thr Ile Arg Ile Ala Gln Pro Lys Leu Ala Lys Pro Val Leu Asp
  1               5                  10                  15

Thr Thr Thr Leu Asn Pro Thr Ile Ala Gly Lys Gly Thr Val Val Ser
                20                  25                  30

Ser Ala Glu Asn Glu Leu Ala Asp Thr Met Gln Ile Val Ser Leu Gln
            35                  40                  45
```

-continued

Leu Asn Lys Met Lys Ser Arg Lys Ser Cys Gly Ile Ala Val Gly Thr
                50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                 85                  90

<210> SEQ ID NO 89
<211> LENGTH: 94
<212> TYPE: PRT
<213> ORGANISM: Chlamydia trachomatis

<400> SEQUENCE: 89

Asp Thr Ile Arg Ile Ala Gln Pro Lys Leu Ala Glu Ala Ile Leu Asp
 1               5                  10                  15

Val Thr Thr Leu Asn Pro Thr Ile Ala Gly Lys Gly Thr Val Val Ala
                20                  25                  30

Ser Gly Ser Asp Asn Asp Leu Ala Asp Thr Met Gln Ile Val Ser Leu
            35                  40                  45

Gln Leu Asn Lys Met Lys Ser Arg Lys Ser Cys Gly Ile Ala Val Gly
        50                  55                  60

Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg
                85                  90

<210> SEQ ID NO 90
<211> LENGTH: 95
<212> TYPE: PRT
<213> ORGANISM: Chlamydia trachomatis

<400> SEQUENCE: 90

Asp Thr Ile Arg Ile Ala Gln Pro Lys Leu Ala Glu Ala Val Leu Asp
 1               5                  10                  15

Val Thr Thr Leu Asn Pro Thr Ile Ala Gly Lys Gly Ser Val Val Ala
                20                  25                  30

Ser Gly Ser Glu Asn Glu Leu Ala Asp Thr Met Gln Ile Val Ser Leu
            35                  40                  45

Gln Leu Asn Lys Met Lys Ser Arg Lys Ser Cys Gly Ile Ala Val Gly
        50                  55                  60

Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg Phe
                85                  90                  95

<210> SEQ ID NO 91
<211> LENGTH: 91
<212> TYPE: PRT
<213> ORGANISM: Chlamydia trachomatis

<400> SEQUENCE: 91

Asp Thr Ile Arg Ile Ala Gln Pro Lys Leu Glu Thr Ser Ile Leu Lys
 1               5                  10                  15

Met Thr Thr Trp Asn Pro Thr Ile Ser Gly Ser Gly Ile Asp Val Asp
                20                  25                  30

Thr Lys Ile Thr Asp Thr Leu Gln Ile Val Ser Leu Gln Leu Asn Lys
            35                  40                  45

Met Lys Ser Arg Lys Ser Cys Leu Ile Ala Ile Gly Thr Thr Ile Val

```
                  50                  55                  60
Asp Ala Asp Lys Tyr Ala Val Thr Val Glu Thr Arg Leu Ile Asp Glu
 65                  70                  75                  80

Arg Ala Ala His Val Asn Ala Gln Phe Arg Phe
                 85                  90

<210> SEQ ID NO 92
<211> LENGTH: 93
<212> TYPE: PRT
<213> ORGANISM: Chlamydia pneumoniae

<400> SEQUENCE: 92

Asp Asn Ile Arg Ile Ala Gln Pro Lys Leu Pro Thr Ala Val Leu Asn
  1               5                  10                  15

Leu Thr Ala Trp Asn Pro Ser Leu Leu Gly Asn Ala Thr Ala Leu Ser
                 20                  25                  30

Thr Thr Asp Ser Phe Ser Asp Phe Met Gln Ile Val Ser Cys Gln Ile
                 35                  40                  45

Asn Lys Phe Lys Ser Arg Lys Ala Cys Val Thr Ala Val Ala Thr Leu
             50                  55                  60

Ile Val Asp Ala Asp Lys Trp Ser Leu Thr Ala Glu Ala Arg Leu Asn
 65                  70                  75                  80

Asp Glu Arg Ala Ala His Ser Gly Ala Gln Phe Arg Phe
                 85                  90

<210> SEQ ID NO 93
<211> LENGTH: 17
<212> TYPE: PRT
<213> ORGANISM: Chlamydia pneumoniae

<400> SEQUENCE: 93

Cys Thr Gly Ser Ala Ala Ala Asn Tyr Thr Thr Ala Val Asp Arg Pro
  1               5                  10                  15

Asn

<210> SEQ ID NO 94
<211> LENGTH: 18
<212> TYPE: PRT
<213> ORGANISM: Chlamydia trachomatis

<400> SEQUENCE: 94

Cys Thr Gly Asp Ala Asp Leu Thr Thr Ala Pro Thr Pro Ala Ser Arg
  1               5                  10                  15

Glu Asn

<210> SEQ ID NO 95
<211> LENGTH: 19
<212> TYPE: PRT
<213> ORGANISM: Chlamydia trachomatis

<400> SEQUENCE: 95

Cys Thr Thr Ala Thr Gly Asn Ala Ala Ala Pro Ser Thr Cys Thr Ala
  1               5                  10                  15

Arg Glu Asn

<210> SEQ ID NO 96
<211> LENGTH: 17
<212> TYPE: PRT
<213> ORGANISM: Chlamydia psitacci
```

```
<400> SEQUENCE: 96

Cys Ala Ser Gly Thr Ala Ser Asn Thr Thr Val Ala Ala Asp Arg Ser
 1               5                  10                  15
Asn

<210> SEQ ID NO 97
<211> LENGTH: 15
<212> TYPE: PRT
<213> ORGANISM: Chlamydia pneumoniae

<400> SEQUENCE: 97

Cys Phe Gly Val Lys Gly Thr Thr Val Asn Ala Asn Glu Leu Pro
 1               5                  10                  15

<210> SEQ ID NO 98
<211> LENGTH: 15
<212> TYPE: PRT
<213> ORGANISM: Chlamydia trachomatis

<400> SEQUENCE: 98

Cys Phe Gly Arg Asp Glu Thr Ala Val Ala Ala Asp Asp Ile Pro
 1               5                  10                  15

<210> SEQ ID NO 99
<211> LENGTH: 18
<212> TYPE: PRT
<213> ORGANISM: Chlamydia trachomatis

<400> SEQUENCE: 99

Cys Phe Gly Asp Asn Glu Asn His Ala Thr Val Ser Asp Ser Lys Leu
 1               5                  10                  15
Val Pro

<210> SEQ ID NO 100
<211> LENGTH: 14
<212> TYPE: PRT
<213> ORGANISM: Chlamydia psitacci

<400> SEQUENCE: 100

Cys Ile Gly Leu Ala Gly Thr Asp Phe Ala Asn Gln Arg Pro
 1               5                  10

<210> SEQ ID NO 101
<211> LENGTH: 13
<212> TYPE: PRT
<213> ORGANISM: Chlamydia pneumoniae

<400> SEQUENCE: 101

Cys Gln Ile Asn Lys Phe Lys Ser Arg Lys Ala Cys Gly
 1               5                  10

<210> SEQ ID NO 102
<211> LENGTH: 13
<212> TYPE: PRT
<213> ORGANISM: Chlamydia trachomatis

<400> SEQUENCE: 102

Cys Gln Ile Asn Lys Met Lys Ser Arg Phe Ala Cys Gly
 1               5                  10

<210> SEQ ID NO 103
<211> LENGTH: 13
<212> TYPE: PRT
```

<213> ORGANISM: Chlamydia trachomatis

<400> SEQUENCE: 103

Cys Gln Leu Asn Lys Met Lys Ser Arg Lys Ala Cys Gly
 1               5                  10

<210> SEQ ID NO 104
<211> LENGTH: 13
<212> TYPE: PRT
<213> ORGANISM: Chlamydia psitacci

<400> SEQUENCE: 104

Cys Gln Ile Asn Lys Phe Lys Ser Arg Phe Ala Cys Gly
 1               5                  10

<210> SEQ ID NO 105
<211> LENGTH: 6
<212> TYPE: PRT
<213> ORGANISM: Chlamydia pneumoniae

<400> SEQUENCE: 105

Arg Lys Lys Glu Arg Ser
 1               5

<210> SEQ ID NO 106
<211> LENGTH: 10
<212> TYPE: PRT
<213> ORGANISM: Chlamydia pneumoniae

<400> SEQUENCE: 106

Ser Thr Glu Cys Asn Ser Gln Ser Pro Gln
 1               5                  10

<210> SEQ ID NO 107
<211> LENGTH: 13
<212> TYPE: PRT
<213> ORGANISM: Ebola virus

<400> SEQUENCE: 107

Asn Pro Asn Leu His Tyr Trp Thr Thr Gln Asp Glu Gly
 1               5                  10

<210> SEQ ID NO 108
<211> LENGTH: 22
<212> TYPE: PRT
<213> ORGANISM: Ebola virus

<400> SEQUENCE: 108

Ser Gly Gln Ser Pro Ala Arg Thr Ser Ser Asp Pro Gly Thr Asn Thr
 1               5                  10                  15

Thr Thr Glu Asp His Lys
                20

<210> SEQ ID NO 109
<211> LENGTH: 9
<212> TYPE: PRT
<213> ORGANISM: Ebola virus

<400> SEQUENCE: 109

Thr Gly Gly Arg Arg Thr Arg Arg Glu
 1               5

<210> SEQ ID NO 110
<211> LENGTH: 10

```
<212> TYPE: PRT
<213> ORGANISM: Ebola virus

<400> SEQUENCE: 110

Arg Asp Arg Phe Lys Arg Thr Ser Phe Phe
 1               5                  10

<210> SEQ ID NO 111
<211> LENGTH: 12
<212> TYPE: PRT
<213> ORGANISM: Ebola virus

<400> SEQUENCE: 111

Glu Gln His His Arg Arg Thr Asp Asn Asp Ser Thr
 1               5                  10

<210> SEQ ID NO 112
<211> LENGTH: 11
<212> TYPE: PRT
<213> ORGANISM: Ebola virus

<400> SEQUENCE: 112

Glu Asn Thr Asn Thr Ser Lys Ser Thr Asp Phe
 1               5                  10

<210> SEQ ID NO 113
<211> LENGTH: 12
<212> TYPE: PRT
<213> ORGANISM: Ebola virus

<400> SEQUENCE: 113

Tyr Thr Ser Gly Lys Arg Ser Asn Thr Thr Gly Lys
 1               5                  10

<210> SEQ ID NO 114
<211> LENGTH: 11
<212> TYPE: PRT
<213> ORGANISM: Ebola virus

<400> SEQUENCE: 114

Thr Thr Thr Ser Pro Gln Asn His Ser Glu Thr
 1               5                  10

<210> SEQ ID NO 115
<211> LENGTH: 11
<212> TYPE: PRT
<213> ORGANISM: Ebola virus

<400> SEQUENCE: 115

Pro Asp Gln Gly Asp Asn Asp Asn Trp Trp Thr
 1               5                  10

<210> SEQ ID NO 116
<211> LENGTH: 12
<212> TYPE: PRT
<213> ORGANISM: Ebola virus

<400> SEQUENCE: 116

Thr Ile Ser Thr Ser Pro Gln Ser Leu Thr Thr Lys
 1               5                  10

<210> SEQ ID NO 117
<211> LENGTH: 16
<212> TYPE: PRT
<213> ORGANISM: Ebola virus
```

```
<400> SEQUENCE: 117

Thr Glu Asp Pro Ser Ser Gly Tyr Tyr Ser Thr Thr Ile Arg Tyr Gln
1               5                   10                  15

<210> SEQ ID NO 118
<211> LENGTH: 15
<212> TYPE: PRT
<213> ORGANISM: Ebola virus

<400> SEQUENCE: 118

Thr His His Gln Asp Thr Gly Glu Glu Ser Ala Ser Ser Gly Lys
1               5                   10                  15
```

IDENTIFICATION OF ANTIGENIC PEPTIDE SEQUENCES

RELATED APPLICATIONS

This application is a continuation-in-part of U.S. patent application Ser. No. 08/911,593, filed Aug. 14, 1997, which claims the benefit of U.S. Provisional Application No. 60/023,921, filed Aug. 14, 1996, the entire teachings of which are incorporated herein by reference.

BACKGROUND OF THE INVENTION

Antibodies are widely used in diagnostic assays in both human and veterinary medicine. Uses include enzyme-linked immunosorbent analysis (ELISA), quantitative antigen capture analysis, radioisotope-tagged reagents for in vivo localization of target antigens, and for in vivo localization of cytotoxic agents to target cells (i.e., immunotoxic therapy). The minimum epitope size for protein antigens is generally considered to be 5–6 amino acids, either as a linear sequence or as non-contiguous amino acids whose spatial placement defines the epitope (i.e., conformational epitope). Specificity is provided by the large number of potential amino acid epitopic sequences possible for a minimum epitope (i.e., $5^{20}$).

Most commonly, large antigens or microbial organisms are used to induce antibody responses in order to insure the presentation of good antigenic sequences in the host animal. The use of these multivalent antigens for the production of polyclonal antibodies generally requires host-based adsorption of the sera to reduce non-specific cross-reactive antibody species. Monoclonal antibodies avoid this pitfall but frequently result in reagents whose specific epitopic specificity is unknown.

SUMMARY OF THE INVENTION

The invention relates to a method of identifying an antigenic amino acid subsequence from within a larger amino acid sequence comprising the steps of evaluating the hydrophilicity of subsequences of an amino acid sequence of interest; evaluating the flexibilitiy of subsequences of the amino acid sequence of interest; and selecting an amino acid subsequence having overlapping regions of hydrophilicity and flexibility. In particular embodiments, the larger amino acid sequence is selected from the group consisting of polypeptides expressed by members of the Chlamydia genus.

The invention also relates to antigenic amino acid subsequences identified by the methods described herein. In particular embodiments, the invention pertains to an antigenic amino acid subsequence selected from the group consisting of SEQ ID NOS: 1–118.

The invention also pertains to antibodies which are specific for the antigenic amino acid subsequences described herein. For example, the invention pertains to monoclonal antibodies specific for antigenic amino acid subsequences described herein.

The invention also relates to diagnostic and therapeutic methods utilizing the described antigenic amino acid subsequences and antibodies thereto.

BRIEF DESCRIPTION OF THE DRAWINGS

Figure 1A:
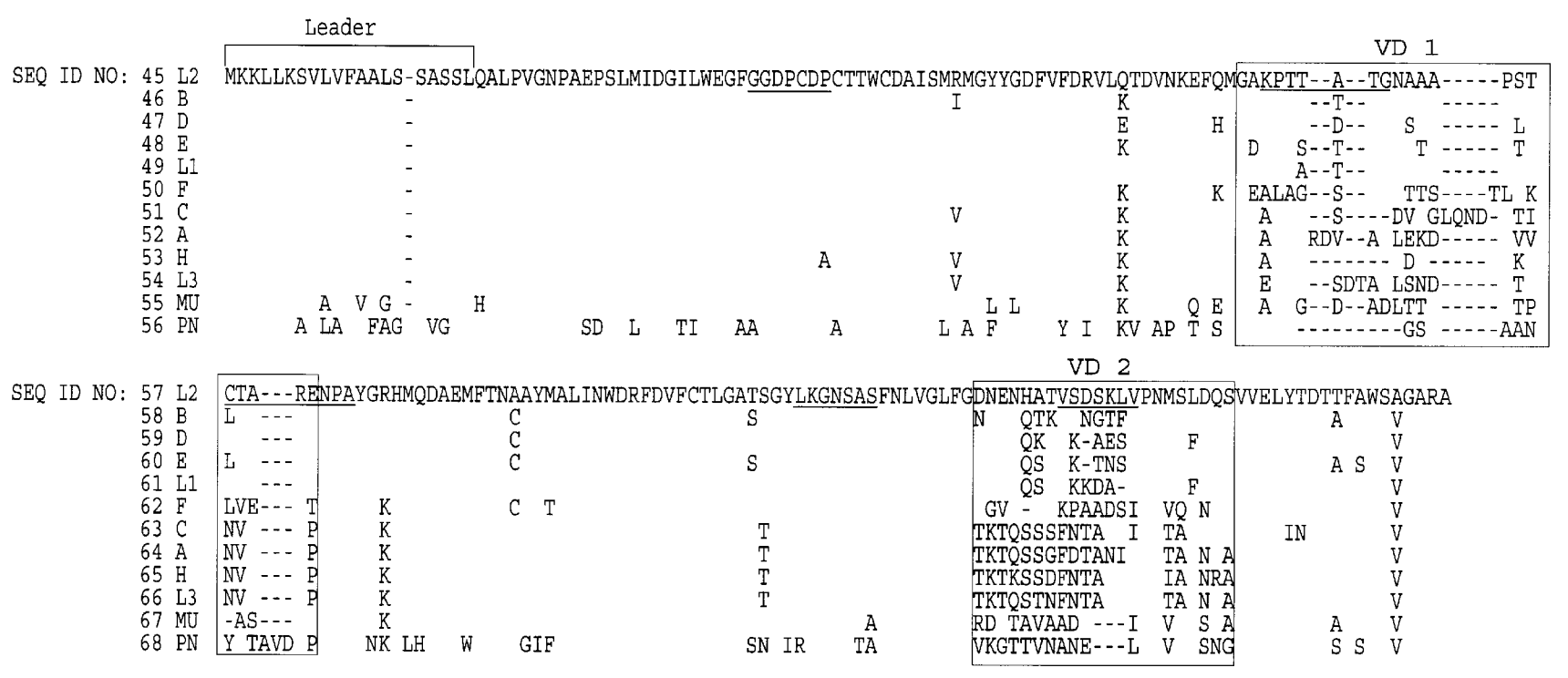

FIGS. 1A and 1B are sequence alignments of various Chlamydia MOMPs. Variable domains (VD1–VD4) are boxed. Sequences are aligned with the L2 serovar of C. trachomatis and are ranked from highest homology (B, D, E, L1) to lower homology (F, C, and A, H, L3). MU is the mouse pneumonitis C. trachomatis. PN refers to the human C. pneumoniae. Deletions are indicated by (−). A blank indicates the same residue as L2. The leader sequence is bracketed. Underlined seven residue segments are predicted to contain the most flexible peptide backbone based on the L2 sequence. Asterisks indicate the most hydrophilic region.

FIG. 2 illustrates the predicted antigenic sequences from variable domains 1 (VD1) of various Chlamydia species. The boxed cysteine (C) residue is not part of the native sequence but has been added at the amino terminus for cross-linking to carrier proteins used in immunization.

FIG. 3 illustrates the predicted antigenic sequences from variable domain 2 (VD2) of various Chlamydia species. The boxed cysteine (C) residue is not part of the native seuqence but has been added at the amino terminus for cross-linking to carrier proteins used in immunization.

FIG. 4 illustrates the predicted antigenic sequences from a common domain of various Chlamydia species. The shaded box indicates hydrophilic mobile region common to each with expected cross-reactivity for antibodies specific for the sequence. The boxed cysteine (C) residue is not part of the native sequence but has been added at the amino terminus for cross-linking to carrier proteins used in immunization.

DETAILED DESCRIPTION OF THE INVENTION

Globular proteins have a hydrophobic core, with the external surfaces bearing relatively hydrophilic sequences. It is these segments in native proteins which are most likely to be recognized by antibodies. Work described herein describes methods for identifying linear amino acid antigenic sequences for the production of both polyclonal and monoclonal antibodies to defined antigenic domains. One significant advantage of this technique is that it provides antibodies to a known epitope of a target antigen or organism.

The identification of antigenic domains described herein is based on the overlap of the most hydrophilic peptide segments of an antigen with those peptide segments with a concomitant predicted peptide flexibility. Increased flexibility allows more conformational degrees of freedom for optimal fit into an antibody binding site. Aromatic amino acids are frequently found in antigenic epitopes although hydrophobic with bulky R groups. This decrease in the relative hydrophobicity and flexibility of the peptide sequence containing the aromatic residue is compensated for if accessible (i.e., surface of the antigen).

The relative hydrophilicity of peptide domains is based on the individual hydrophilicity of each amino acid in six or more residue segments as defined by Hopp and Woods (Hopp and Woods, *Proceedings of National Academy of Sciences USA* 78:3824–3828). Flexibility of the peptide chain at each Cα residue is measured from the average value of the atomic temperature factor as affected by adjacent residues. Amino acids which result in rigidity of the chain include alanine, valine, leucine, isoleucine, tyrosine, phenylalanine, tryptophan, cysteine, methionine, and histidine. Flexibility is computed by averaging the rigidity factor (B value) along a seven residue segment using the following expression (Karplus and Shulz, *Naturwissenschaften* 72:212–213 (1985); Van Regenmortel, *Trends in Biochemical Sciences* (TIBS) 12:36–39 (1986)):

$$F = B_i + 0.75(B_{i-1} + B_{i+1}) + 0.5(B_{i-2} + B_{i+2}) + 0.25(B_{i-3} + B_{i+3})$$

With respect to identification of larger proteins or polypeptides from which the antigenic amino acid subsequences are selected, bands idenitifed by gel analysis can be isolated and purified by HPLC, and the resulting purified protein can be sequenced. Alternatively, the purified protein can be enzymatically digested by methods known in the art to produce polypeptide fragments which can be sequenced. The sequencing can be performed, for example, by the methods of Wilm et al. (*Nature* 379(6564):466–469 (1996)). The protein can be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice*, 2nd Edition, Springer-Verlag, New York (1987); and Deutscher (ed), *Guide to Protein Purification, Methods in Enzymology*, Vol. 182 (1990). If the protein is secreted, it can be isolated from the supernatant in which the host cell is grown. If not secreted, the protein can be isolated from a lysate of the host cells.

In addition to substantially full-length polypeptides used as the source of the selected antigenic amino acid subsequences, biologically active fragments of polypeptides, or analogs thereof, including organic molecules which simulate the interactions of the polypeptides, can be used. Biologically active fragments include any portion of the full-length polypeptide which has a biological function, including ligand binding, and antibody binding. Ligand binding includes binding by nucleic acids, proteins or polypeptides, small biologically active molecules, or large cellular structures. Amino acid sequences identified as antigenic from de novo sequence determination of CDNA reading frames or the isolated protein of interest, or by established sequences from GeneBank and the (PDB), can be most conveniently synthesized by solid phase peptide synthesis using either standard F-Monc or t-Boc methodologies.

This invention also pertains to an isolated polypeptide comprising the antigenic amino acid subsequences of the invention. The encoded proteins or polypeptides of the invention can be partially or substantially purified (e.g., purified to homogeneity), and/or are substantially free of other proteins. According to the invention, the amino acid sequence of the polypeptide can be that of the naturally-occurring polypeptide or can comprise alterations herein. Such alterations include conservative or non-conservative amino acid substitutions, additions and deletions of one or more amino acids; however, such alterations should preserve at least one activity of the encoded protein or polypeptide, i.e., the altered or mutant protein should be an active derivative of the naturally-occurring protein. For example, the mutation(s) can preferably preserve the three dimensional configuration of the binding and/or catalytic site of the native protein, the hydrophilicity and/or flexibility of the polypeptide. The presence or absence of biological activity or activities can be determined by various functional assays as described herein. Moreover, amino acids which are essential for antigenicity or the function of the encoded protein or polypeptide can be identified by methods known in the art. Particularly useful methods include identification of conserved amino acids in the family or subfamily, site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity and antigenicity, as described herein.

Specifically, appropriate amino acid alterations can be made on the basis of several criteria, including hydrophobicity, hydrophilicity, basic or acidic character, charge, polarity, size, the presence or absence of a functional group (e.g., —SH or a glycosylation site), rigidity or flexibility, and aromatic character. Assignment of various amino acids to similar groups based on the properties above will be readily apparent to the skilled artisan; further appropriate amino acid changes can also be found in Bowie et al. (*Science* 247:1306–1310(1990)).

Polypeptides of the invention can also be a fusion protein comprising all or a portion of the amino acid sequence fused to an additional component. Additional components, such as radioisotopes and antigenic tags, can be selected to assist in the isolation or purification of the polypeptide or to extend the half life of the polypeptide; for example, a hexahistidine tag would permit ready purification by nickel chromatography. Polypeptides or amino acid sequences described herein can be isolated from naturally-occurring sources, chemically synthesized or recombinantly produced by methods known in the art.

The present invention also relates to nucleotide sequences (nucleic acid molecules) which encode the antigenic amino acid subsequences or polypeptides of the invention. As appropriate, nucleic acid molecules of the present invention can be RNA, for example, mRNA, or DNA, such as CDNA and genomic DNA. DNA molecules can be double-stranded or single-stranded; single stranded RNA or DNA can be either the coding, or sense, strand or the non-coding, or antisense, strand. The nucleic acid molecule can include all or a portion of the coding sequence of a gene and can further comprise additional non-coding sequences such as introns and non-coding 3' and 5' sequences (including regulatory sequences, for example). Additionally, the nucleic acid molecule can be fused to a marker sequence, for example, a sequence which encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from influenza.

As used herein, an "isolated" gene or nucleic acid molecule is intended to mean a gene or nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Recombinant DNA contained in a vector are included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue such as liver tissue), such as by Northern blot analysis.

The invention also pertains to nucleic acid molecules which hybridize under high stringency hybridization conditions (e.g., for selective hybridization) to a nucleotide sequence described herein. Hybridization probes are oligonucleotides which bind in a base-specific manner to a complementary strand of nucleic acid. Appropriate stringency conditions are known to those skilled in the art or can be found in standard texts such as *Current Protocols in Molecular Biology*, John Wiley & Sons, N.Y. (1989), 6.3.1–6.3.6. For example, stringent hybridization conditions include a salt concentration of no more than 1 M and a temperature of at least 25° C. In one embodiment, conditions of 5×SSPE (750 mM NaCl, 50 mM NaPhosphate, 5 mM EDTA, pH 7.4) and a temperature of 25–30° C., or equivalent conditions, are suitable for specific probe hybridizations. Equivalent conditions can be determined by varying one or more of the parameters given as an example, as known in the art, while maintaining a similar degree of identity or similarity between the target nucleic acid molecule and the primer or probe used. Hybridizable nucleic acid molecules are useful as probes and primers for diagnostic applications.

Accordingly, the invention pertains to nucleic acid molecules which have a substantial identity with the nucleic acid molecules described herein and which encode antigenic amino acid sequences; particularly preferred are nucleic acid molecules which have at least about 90%, and more preferably at least about 95% identity with nucleic acid molecules described herein. Thus, DNA molecules which comprise a sequence which is different from the naturally-occurring nucleic acid molecule but which, due to the degeneracy of the genetic code, encode the same polypeptide are the subject of this invention. The invention also encompasses variations of the nucleic acid molecules of the invention, such as those encoding portions, analogues or derivatives of the encoded polypeptide. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent; that is, they do not alter the characteristics or activity of the encoded protein or polypeptide. As used herein, activities of the encoded protein or polypeptide include, but are not limited to, catalytic activity, binding function, antigenic function and oligomerization function.

The nucleotide sequences described herein can be amplified as needed by methods known in the art. For example, this can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a cDNA library. Corresponding clones can be isolated, DNA can obtained following in vivo excision, and the cloned insert can be sequenced in either or both orientations by art recognized methods, to identify the correct reading frame encoding a protein of the appropriate molecular weight. For example, the direct analysis of the nucleotide sequence of nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Taboratory Manual*, (Acad. Press, 1988)). Using these or similar methods, the polypeptide(s) and the DNA encoding the polypeptide can be isolated, sequenced and further characterized.

The invention also provides expression vectors containing a nucleic acid sequence described herein, operably linked to at least one regulatory sequence. Many such vectors are commercially available, and other suitable vectors can be readily prepared by the skilled artisan. "Operably linked" is intended to mean that the nucleic acid molecule is linked to a regulatory sequence in a manner which allows expression of the nucleic acid sequence. Regulatory sequences are art-recognized and are selected to produce the encoded polypeptide. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of polypeptide desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains, Streptomyces, Pseudomonas, *Serratia marcescens* and *Salmonella typhimurium*, insect cells (baculovirus), including Drosophila, fungal cells, such as yeast cells, plant cells and mammalian cells, such as thymocytes, Chinese hamster ovary cells (CHO), and COS cells.

Thus, a nucleic acid molecule described herein can be used to produce a recombinant form of the polypeptide via microbial or eukaryotic cellular processes. Ligating the polynucleic acid molecule into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant polypeptides according to the present invention by microbial means or tissue-culture technology. Accordingly, the invention pertains to the production of encoded polypeptides by recombinant technology.

The polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind an antigenic amino acid sequence or subsequence of the invention. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); Internaticnal Patent Application WO86/01533 (Neuberger); and U.S. Pat. No. 5,225,539 (Winters)) which bind to the described amino acid sequence or subsequence are within the scope of the invention. A mammal, such as a mouse, rat, hamster or rabbit, can be immunized with an immunogenic form of the amino acid subsequence. Techniques for conferring immunogenicity on a polypeptide include conjugation to carriers or other techniques well known in the art. The polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monocloilal Antibodies and Cancer Therapy*, Alan R. Liss, Inc., pp. 77–96 (1985)). The term "antibody" as used herein is intended to include fragments thereof, such as Fab and F(ab)$_2$ and antigen binding fragments. Antibodies described herein can be used to inhibit the activity of the polypeptides and proteins described herein, particularly in vitro and in cell extracts, using methods known in the art.

Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the protein or polypeptide. Tissue samples which can be assayed include human tissues, e.g., differentiated and non-differentiated cells. Examples include bone marrow, thymus, kidney, liver, brain, pancreas, fibroblasts and epithelium. These antibodies are useful in diagnostic assays, or as an active ingredient in a pharmaceutical composition.

The invention also relates to immunogenic compositions comprising amino acid sequences described herein, as well as vaccine compositions comprising polypeptides or antibodies described herein. Peptides and antibodies identified by methods described herein can also be used in a variety of assay and protein processing applications, including, but not limited to, radioimmunoassays, ELISA, antigen capture assays, competitive inhibition assays, affinity chromatography, Western Blotting, Labeled-antibody assays such as immunoflorescence assays, immunohistochemical staining assays and immunoprecipitation assays. The antiobdies, alone or linked to particular toxins, can also be used for a variety of therapeutic and other purposes, inclduing removing specific lymphocyte subsets, inhibiting cell function, inhibiting graft rejection, alleviating or suppressing autoimmune disease, and attaching to tumors.

The present invention also pertains to pharmaceutical compositions comprising antigenic amino acid sequences or subsequences and other antibodies described herein. For instance, a composition of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices and slow release polymeric devices. The pharmaceutical compositions of this invention can also be administered as part of a combinatorial therapy with other agents.

The nucleic acid sequences described herein can also be used for genetic immunization. The term, "genetic immunization", as used herein, refers to inoculation of a vertebrate, particularly a mammal, with a nucleic acid vaccine directed against a pathogenic agent, such as Chlamydia, resulting in protection of the vertebrate against the pathogenic agent. Representative vertebrates include mice, dogs, cats, chickens, sheep, goats, cows, horses, pigs, non-human primates, and humans. A "nucleic acid vaccine" or "DNA vaccine" as used herein, is a nucleic acid construct comprising a polynucleotide encoding a polypeptide antigen, particularly an antigenic amino acid subsequence identified by methods described herein. The nucleic acid construct can also include transcriptional promoter elements, enhancer elements, splicing signals, termination and polyadenylation signals, and other nucleic acid sequences.

"Protection against the pathogenic agent" as used herein refers to generation of an immune response in the vertebrate, the immune response being protective (partially or totally) against manifestations of the disease caused by the pathogenic agent. A vertebrate that is protected against disease may be infected with the pathogenic agent, but to a lesser degree than would occur without immunization; may be infected with the pathogenic agent, but does not exhibit disease symptoms; or may be infected with the pathogenic agent, but exhibits fewer disease symptoms than would occur without immunization. Alternatively, the vertebrate that is protected against disease may not become infected with the pathogenic agent at all, despite exposure to the agent.

The nucleic acid vaccine can be produced by standard methods. For example, using known methods, a nucleic acid encoding polypeptide antigen of interest, e.g., DNA encoding an antigenic amino acid subsequence, can be inserted into an expression vector to construct a nucleic acid vaccine (see Maniatis et al., *Molecular Cloning, A Laboratory Manual*, 2nd edition, Cold Spring Harbor Laboratory Press (1989)).

The individual vertebrate is inoculated with the nucleic acid vaccine (i.e., the nucleic acid vaccine is administered), using standard methods. The vertebrate can be inoculated subcutaneously, intravenously, intraperitoneally, intradermally, intramuscularly, topically, orally, rectally, nasally, buccally, vaginally, by inhalation spray, or via an implanted reservoir in dosage formulations containing conventional non-toxic, physiologically acceptable carriers or vehicles. Alternatively, in a preferred embodiment, the vertebrate is innoculated with the nucleic acid vaccine through the use of a particle acceleration instrument (a "gene gun"). The form in which it is administered (e.g., capsule, tablet, solution, emulsion) will depend in part on the route by which it is administered. For example, for mucosal administration, nose drops, inhalants or suppositories can be used.

The nucleic acid vaccine can be administered in conjunction with known adjuvants. The adjuvant is administered in a sufficient amount, which is that amount that is sufficient to generate an enhanced immune response to the nucleic acid vaccine. The adjuvant can be administered prior to (e.g., 1 or more days before) inoculation with the nucleic acid vaccine; concurrently with (e.g., within 24 hours of) inoculation with the nucleic acid vaccine; contemporaneously (simultaneously) with the nucleic acid vaccine (e.g., the adjuvant is mixed with the nucleic acid vaccine, and the mixture is administered to the vertebrate); or after (e.g., 1 or more days after) inoculation with the nucleic acid vaccine. The adjuvant can also be administered at more than one time (e.g., prior to inoculation with the nucleic acid vaccine and also after inoculation with the nucleic acid vaccine). As used herein, the term "in conjunction with" encompasses any time period, including those specifically described herein and combinations of the time periods specifically described herein, during which the adjuvant can be administered so as to generate an enhanced immune response to the nucleic acid vaccine (e.g., an increased antibody titer to the antigen encoded by the nucleic acid vaccine, or an increased antibody titer to the pathogenic agent). The adjuvant and the nucleic acid vaccine can be administered at approximately the same location on the vertebrate; for example, both the adjuvant and the nucleic acid vaccine are administered at a marked site on a limb of the vertebrate.

In a particular embodiment, the nucleic acid construct is co-administered with a transfection-facilitating cationic lipid. In a preferred embodiment, the cationic lipid is dioctylglycylspermine (DOGS). PCT application publication no. WO 96/21356). In a particular embodiment, the nucleic acid construct is co-administered with a transfection-facilitating cationic lipid and an amount of 1,25(OH)$_2$D3 effective to produce a mucosal response. In a preferred embodiment, the nucleic acid construct is complexed with a transfection-facilitating cationic lipid.

The teachings of all references cited herein are are speeifically incorporated herein by reference. The teachings of copending U.S. patent application Ser. No. 09/025,521, entitled "Diagnosis and Management of Infection Caused by Chlamydia" by William M. Mitchell and Charles W. Stratton, filed concurrently with the present application, are also incorporated herein by reference in their entirety.

EXAMPLES

Examples of the Predictive power of the Methodology Described Herein Include the Following 1) Antigenicity of the MOMP (major outer membrane protein) of Chlamydia:

In order to provide ELISA assays that are species- and potentially strain-specific for the various Chlamydia, two regions in the MOMP have been identified which show minimal amino acid sequence homologies and which are predicted to be excellent antigenic domains by virtue of hydrophilicity and peptide mobility on the solvent-accessible surface of MOMP. FIG. 1 illustrates the constant and variable domain (VD) of the various chlamydial species. The identified species-specific antigenic domains are located in VD1 and VD2. FIG. 2 illustrates the peptide amino acid sequences employed for the construction of peptide based ELISAs with species specificity for VD1. FIG. 3 illustrates the peptides for VD2 which are used similarly to the VD1 sequences. In addition, a highly antigenic domain (FIG. 4) common to all Chlamydia has been identified and developed as genus-specific ELISA for the Chlamydia. Immunization of rabbits has verified the antigenicity of each peptide to each peptide (Table 1). Monoclonal antibodies have further verified the specificities and antigenicity of each peptide (Table 1) as predicted by computer analysis of the nucleotide-generated amino acid sequence of each species-specific MOMP.

TABLE 1

Antigenic Responses To Peptides From Four Species Of Chlamydiae Identified By Hydrophilicity And Peptide Movement As Highly Antigenic

| Chlamydiae Species | Peptide[b] | Titer[a] Pre | Post |
|---|---|---|---|
| c. pneumoniae | 90–105 | 100 | >3200 |
| c. trachomatis L2 | 91–106 | 800 | >3200 |
| c. psittaci | 92–106 | 400 | >3200 |
| c. trachomatis (mouse) | 89–105 | 0 | >3200 |
| c. pneumoniae | 158–171 | 25 | >3200 |
| c. trachomatis L2 | 159–175 | 200 | >3200 |
| c. psittaci | 160–172 | 100 | >3200 |
| c. trachomatis (mouse) | 158–171 | 800 | >3200 |
| c. pneumoniae | 342–354 | 200 | >3200 |
| c. trachomatis L2 | 342–354 | 100 | >3200 |
| c. psittaci | ND[c] | | |
| c. trachomatis (mouse) | ND[c] | | |

[a]Reciprocal titer
[b]Immunogenic peptide and ELISA antigen of specific amino acid sequence against the indicated pre-immunization and post-immunization rabbit serum
[c]ND, not done Table 2 illustrates reciprocal titers of a polyclonal and monoclonal antibody against *C. trachomatis* cross-reactive against a *C. pneumoniae* peptide encompassing amino acids 342–354 and a recombinant full length MOMP from *C. pneumoniae*. Note that the monoclonal antibody raised against *C. trachomatis* has as its epitope genus-specific reactivity against peptide 342–354 of *C. pneumoniae*.

TABLE 2

| Antigen | Titer[a] | |
|---|---|---|
| | Polyclonal Ab[b] | Monoclonal Ab[c] |
| CPN Momp[d] | 400 | 0 |
| CPN 90–105[e] | 50 | 0 |
| CPN 158–171[f] | 50 | 0 |
| CPN 342–354[g] | >3200 | 1600 |

[a]Reciprocal titer
[b]Polyclonal goat Ab from Chemicon International, Inc. (Temecula, CA) against MOMP of C. trachomatis
[c]Monoclonal Ab from ICN Immunologicals (Costa Mesa, CA) against MOMP of C. trachomatis
[d]C. pneumoniae recombinant MOMP
[e]Amino acid peptide 90–105 of C. pneumoniae
[f]Amino acid peptide 158–171 of C. pneumoniae
[g]Amino acid peptide 342–354 of C. pneumoniae 2) Antigenicity of the 76 kD Protein of *C. pneumoniae*:

*C. pneumoniae* expresses a gene encoding a unique 76 kD protein (Perez-Melgosa et al., *Infect. Immun.* 62:880–886 (1994)). Hydrophilicity/peptide flexibility analysis predicts the sequence of amino acids 302–315 (KPKESKTDSVERWS; SEQ ID NO: 1) to be highly antigenic; the peptide has been extended towards the carboxyl terminus to include aromatic and additional hydrophilic amino acid residues. The predicted sequence has been further modified to include an adjacent relatively hydrophilic region containing an aromatic amino acid (tryptophan). Other potential antigenic peptides based on either hydrophilicity or peptide flexibility and extended to include emino acids found in hydrophilic or flexible segments, as well as inclusion of aromatic amino acids immediately adjacent to the predicted antigens, are illustrated in Table 3.

TABLE 3 a) Peptide Movement Predictions

| | | |
|---|---|---|
| SSNSSSSTSRS | (SEQ ID NO: 2) | AA 335–345 |
| GSKQQGSS | (SEQ ID NO: 3) | AA 599–606 |
| GKAGQQQG | (SEQ ID NO: 4) | AA 683–690 |
| PSETSTTEK | (SEQ ID NO: 5) | AA 35–43 |
| KPADGSDV | (SEQ ID NO: 6) | AA 583–590 |
| NGQKKPLYLYG | (SEQ ID NO: 7) | AA 70–80 |
| SDVPNPGTTVGGSKQQGSS | (SEQ ID NO: 8) | AA 588–606 |
| HMFNTENPDSQAAQQ | (SEQ ID NO: 9) | AA 636–650 | b) Hydrophilic Prediction

| | | |
|---|---|---|
| DDAENETAS | (SEQ ID NO: 10) | AA 617–625 |

3) Antigenicity of the Chlamydial Heat Shock Proteins:

*C. pneumoniae* expesses three known genes with significant homology to the human heat shock proteins of 70, 60 and 10 kD. Antigenicity of homologous regions may result in molecular mimicry and autoimmunity. Indeed, it is postulated that the tubal scarring secondary to infection from *C. trachomatis* is due to cross-reactive cell mediated immunity against one or more heat shock proteins.

a) *C. pneumonia* DNAK/heatshock Protein 70:

Hydrophilicity/peptide flexibility analysis predicts a highly antigenic sequence in the C-terminal region of the expressed protein. This antigenic domain and its homologous human protein are illustrated in Table 4; vertical lines indicate residue homology while "+" signs indicate retention of a positive charge at the site. Amino acid residues 522–529 are either homologous to the human protein or possess preservation of charge (i.e., AA 525–529). Antibodies against this epitope would be expected to possess cross-reactivity with the human 70 kD heat shock protein. Peptides incorporating the C-terminal end of this common region with the non-homologous sequence would be expected to identify Chlamydial-specific antibodies. Two embodiments of this invention include the full length peptide (AA 521–536) and the Chlamydial-specific epitopic sequence identified as AA 527–536 or truncated for the identification of Chlamydia-specific antibodies. Table 5 illustrates other potential antigenic sequences for the DNAK protein expressed by *C. pneumoniae* based on either peptide flexibility or hydrophilicity and extended to include amino acids found in adjacent hydrophilic or flexible segments, as well as inclusion of aromatic amino acids immediately adjacent to the predicted antigens.

TABLE 4

| | | |
|---|---|---|
| C. pneumoniae (AA 521–536) | KEEDKKRREASDAKNE \|\|\|++++\| \| | (SEQ ID NO: 11) |
| human hsp70 (AA 569–584) | AEEDRRKKERVEAVNM | (SEQ ID NO: 12) |

TABLE 5

| | | |
|---|---|---|
| KKHSFSTKPPSNNGSSEDHIEE | (SEQ ID NO: 13) | (AA 628–649) |
| YTVTSGSKGDAVFE | (SEQ ID NO: 14) | (AA 94–107) |
| TSSEGTRTTPS | (SEQ ID NO: 15) | (AA 34–44) |
| SEHKKSSK | (SEQ ID NO: 16) | (AA 2–9) |
| KDVASGKEQKIRIE | (SEQ ID NO: 17) | (AA 487–500) |
| ERNTTIPTQKKQIFST | (SEQ ID NO: 18) | (AA 411–426) |
| YFNDSQRASSTKDAGR | (SEQ ID NO: 19) | (AA 148–162) |
| EEFKKQEGIDLSKDN | (SEQ ID NO: 20) | (AA 240–254) |
| NAKGGPNINTED | (SEQ ID NO: 21) | (AA 615–626) |
| GERPMAKDNKEIGRFD | (SEQ ID NO: 22) | (AA 441–456) | b) *C. pneumoniae* GROEL/Heatshock Protein (hsp 60) 60:

Two peptides expressed by the GROEL gene of *C. pneumoniae* have a high correlation of hydrophilicity and segment mobility (Table 6). Residues with similar negative charges are identified by "*" symbols. The sequences are highly conserved between *C. pneumoniae* heat shock protein (hsp) 60 and the human hsp 60 associated with the mitochondrion. Thus the potential for molecular mimicry is high and is a likely site for the development of humoral autoimmune responses. Other potential antigenic regions based on either peptide flexibility or hydrophilicity and extended to include amino acids found in adjacent hydrophilic or flexible peptide segments, as well as inclusion of aromatic amino acids immediately adjacent to the predicted areas, are illustrated in Table 7.

TABLE 6

| | | |
|---|---|---|
| C. pneumoniae hsp 60 (AA 385–398) | TEIEMKEKKDRVDD  * \|  \|\|\|\|\|\| \| | (SEQ ID NO: 23) |
| human hsp 60 (AA 410–423) | SDVEVNEKKDRVTD | (SEQ ID NO: 24) |

TABLE 6-continued

| | | |
|---|---|---|
| C. pneumoniae hsp 60 (AA 354–364) | EDSTSDYDKEK<br>* \|\|*\|*\|\|\| | (SEQ ID NO: 25) |
| human hsp 60 (AA 410–420) | DVTTSEYEKEK | (SEQ ID NO: 26) |

TABLE 7

| | | |
|---|---|---|
| DDKSSSA | (SEQ ID NO: 27) | (AA 528–534) |
| KKQIEDSTSDYVSEE | (SEQ ID NO: 28) | (AA 350–364) |
| SSYFSTNPETQE | (SEQ ID NO: 29) | (AA 201–212) |
| EKVGKNGSITVEEADK | (SEQ ID NO: 30) | (AA 167–182) |
| SKTADKAGDGTTTAT | (SEQ ID NO: 31) | (AA 79–93) | c) *C. pneumoniae* GROES/Heat Shock Protein 10 (hsp 10):

Three peptides are highly correlated with respect to hydrophilicity/peptide movement analysis. Comparison to mouse chaperonin 10 indicates little homology of these bacterial antigenic domains with *C. pneumoniae* hsp 10 (Table 8).

TABLE 8

| | | |
|---|---|---|
| C. pneumoniae (AA 20–29) | KREEEEATAR<br>\| \| + | (SEQ ID NO: 32) |
| mouse chaperonin 10 (AA 19–28) | ERSAAETVTK | (SEQ ID NO: 33) |
| C. pneumoniae (AA 36–46) | DTAKKKQDRAE<br>* \| \| | (SEQ ID NO: 34) |
| mouse chaperonin 10 (AA 35–45) | EKSQGKVLQAT | (SEQ ID NO: 35) |
| C. pneumoniae (AA 51–60) | GTGKRTDDGT<br>\| \| + \| | (SEQ ID NO: 36) |
| mouse chaperonin 10 (AA 50–59) | GSGGKGKSGE | (SEQ ID NO: 37) |

4) Antigenicity of the Crysteine-rich Proteins of *C. pneumoniae* a) 60 kD/OMP B:

The second most abundant protein of the external matrix is a 60 kD protein containing 34 cysteines (6.1%). Table 9 illustrates the single peptide domain with overlapping hydrophilicity and peptide flexibility profiles. The sequence has been extended towards the C-terminus to include additional hydrophilic amino acids and two aromatic residues.

Table 10 illustrates several additional peptides with potential antigenic profiles based on either peptide flexibility or hydrophilicity and extended to include amino acids found in adjacent hydrophilic or flexible peptide segments as well as inclusion of aromatic acids immediately adjacent to the predicted areas.

TABLE 9

| | |
|---|---|
| RRNKQPVEQKSRGAFCDKEFYPCEE (AA 60–84) | (SEQ ID NO: 38) |

TABLE 10

| | | |
|---|---|---|
| DMRPGDKKVFTVEFCPQRR | (SEQ ID NO: 39) | (AA 278–296) |
| SSDPETTPTSDGKVWKIDR | (SEQ ID NO: 40) | (AA 157–176) |
| TSESNCGTCTSCAETTTHWK | (SEQ ID NO: 41) | (AA 418–437) |
| KLGSKESVEFS | (SEQ ID NO: 42) | (AA 511–521) |
| TVYRICVTNRGSAEDT | (SEQ ID NO: 43) | (AA 459–474) |
| EYSISVSNPGD | (SEQ ID NO: 44) | (AA 343–353) | b) 9 kD Protein:

This small protein contains 14 cysteines (15.5%). Table 11 illustrates the predicted antigenic sites. Peptide 1 represents the single peptide for the 9 kD cysteine-rich protein identified by common hydrophilic/peptide flexibility profiles. Peptide 2 recognized initially by its peptide flexibility and extended towards the amino terminal to include several hydrophilic residues.

TABLE 11

| | | |
|---|---|---|
| Peptide 1: | RKKERS | (SEQ ID NO: 105) (AA 44–49) |
| Peptide 2: | STECNSQSPQ | (SEQ ID NO: 106) (AA 68–77) |

5) Antigenicity of the Ebola Virus GP Protein:

The GP protein associates into trimers on the surface of the virus and functions as an attachment protein. Two peptides are predicted to be excellent antigens on the basis of overlapping hydrophilic/peptide flexibility profiles (Table 12). Additional potential antigenic sites initially based on either peptide flexibility or hydrophilicity and extended to include amino acids found in adjacent hydrophilic or flexible peptide segments as well as inclusion of aromatic amino acids immediately adjacent to the predicted domains are illustrated in Table 13.

TABLE 12

| | |
|---|---|
| NPNLHYWTTQDEG (AA 512–524) | (SEQ ID NO: 107) |
| SGQSPARTSSDPGTNTTTEDHK (AA 320–340) | (SEQ ID NO: 108) |

TABLE 13

| | | |
|---|---|---|
| TGGRRTRRE | (SEQ ID NO: 109) | (AA 494–502) |
| RDRFKRTSFF | (SEQ ID NO: 110) | (AA 11–21) |
| EQHHRRTDNDST | (SEQ ID NO: 111) | (AA 405–416) |
| ENTNTSKSTDF | (SEQ ID NO: 112) | (AA 433–443) |
| YTSGKRSNTTGK | (SEQ ID NO: 113) | (AA 261–272) |
| TTTSPQNHSET | (SEQ ID NO: 114) | (AA 448–458) |
| PDQGDNDNWWT | (SEQ ID NO: 115) | (AA 636–646) |
| TISTSPQSLTTK | (SEQ ID NO: 116) | (AA 370–381) |
| TEDPSSGYYSTTIRYQ | (SEQ ID NO: 117) | (AA 206–221) |
| THHQDTGEESASSGK | (SEQ ID NO: 118) | (AA 464–478) |

EQUIVALENTS

Those skilled in the art will recognize, or be able to ascertain, using no more than routine experimentation many equivalents to the specific embodiments of the invention described herein. Such equivalents are intended to be encompassed by the following claims:

We claim:

1. A substantially pure immunogenic polypeptide having a sequence consisting essentially of SEQ ID NO: 68 or a subsequence of SEQ ID NO: 68 that comprises amino acids 2 to 14 of SEQ ID NO: 97.

2. The substantially pure immunogenic polypeptide of claim 1, wherein said sequence consists essentially of SEQ ID NO: 68 or amino acids 2 to 14 of SEQ ID NO: 97.

* * * * *

UNITED STATES PATENT AND TRADEMARK OFFICE
CERTIFICATE OF CORRECTION

PATENT NO. : 6,340,463 B1
DATED : January 22, 2002
INVENTOR(S) : William M. Mitchell and Charles W. Stratton It is certified that error appears in the above-identified patent and that said Letters Patent is hereby corrected as shown below:

Column 2,
Line 15, delete "seuqence" and insert -- sequence --.

Column 3,
Line 32, delete "CDNA" and insert -- cDNA --.
Line 45, delete "herein" and insert -- therein --.

Column 4,
Line 26, delete "CDNA" and insert -- cDNA --.
Line 53, delete "circumstance" and insert -- circumstances --.

Column 6,
Line 22, delete "Taboratory" and insert -- Laboratory --.

Column 7,
Line 30, delete "Internaticnal" and insert -- International --.
Line 50, delete "Monocloilal" and insert -- Monoclonal --.

Column 8,
Line 12, delete "antiobdies" and insert -- antibodies --.

Column 9,
Line 18, delete "innoculated" and insert --inoculated --.
Lines 61-62, delete "spcefically" and insert -- specifically --.

Column 10,
Line 30, delete "Monoclional" and insert -- Monoclonal --.

UNITED STATES PATENT AND TRADEMARK OFFICE
CERTIFICATE OF CORRECTION

PATENT NO. : 6,340,463 B1
DATED : January 22, 2002
INVENTOR(S) : William M. Mitchell and Charles W. Stratton It is certified that error appears in the above-identified patent and that said Letters Patent is hereby corrected as shown below:

Column 11,
Line 31, delete "emino" and insert -- amino --.
Line 58, delete "C. pneumonia" and insert -- C. pneumoniae --.

Signed and Sealed this

Twenty-second Day of October, 2002

*Attest:*

*Attesting Officer*

JAMES E. ROGAN
*Director of the United States Patent and Trademark Office*